(12) United States Patent
Emrick et al.

(10) Patent No.: US 10,995,094 B2
(45) Date of Patent: *May 4, 2021

(54) TEMOZOLOMIDE COMPOUNDS, POLYMERS PREPARED THEREFROM, AND METHOD OF TREATING A DISEASE

(71) Applicant: The University of Massachusetts, Boston, MA (US)

(72) Inventors: Todd Emrick, South Deerfield, MA (US); Matthew Skinner, Amherst, MA (US); Sarah M. Ward, Amherst, MA (US); Banishree Saha, Greenfield, MA (US)

(73) Assignee: THE UNIVERSITY OF MASSACHUSETTS, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/735,910

(22) Filed: Jan. 7, 2020

(65) Prior Publication Data

US 2020/0140448 A1 May 7, 2020

Related U.S. Application Data

(63) Continuation of application No. 15/709,862, filed on Sep. 20, 2017, now Pat. No. 10,562,901.

(60) Provisional application No. 62/398,078, filed on Sep. 22, 2016.

(51) Int. Cl.
| | |
|---|---|
| *C07D 257/12* | (2006.01) |
| *C07D 487/04* | (2006.01) |
| *A61K 31/787* | (2006.01) |
| *C08F 22/10* | (2006.01) |
| *A61K 47/54* | (2017.01) |
| *C08G 65/32* | (2006.01) |
| *A61K 47/60* | (2017.01) |
| *A61K 47/58* | (2017.01) |

(52) U.S. Cl.
CPC .......... *C07D 487/04* (2013.01); *A61K 31/787* (2013.01); *A61K 47/545* (2017.08); *A61K 47/58* (2017.08); *A61K 47/60* (2017.08); *C08F 22/10* (2013.01); *C08G 65/32* (2013.01)

(58) Field of Classification Search
CPC .... C07D 487/04; A61K 31/787; A61K 47/60; A61K 47/58; A61K 47/545; C08F 22/10
See application file for complete search history.

(56) References Cited

U.S. PATENT DOCUMENTS

| | | | |
|---|---|---|---|
| 2006/0047117 A1 | 3/2006 | Wang et al. | |
| 2012/0328555 A1 | 12/2012 | Patil et al. | |
| 2013/0210877 A1* | 8/2013 | Chen .................... | A61K 47/542 |
| | | | 514/393 |

FOREIGN PATENT DOCUMENTS

| | | | |
|---|---|---|---|
| CN | 1485327 | * | 3/2004 |
| WO | 2010149968 A1 | | 12/2010 |

OTHER PUBLICATIONS

Li et al., J Neurooncol, 2014, pp. 25-30.*
Adamson, C., et al., "Glioblastoma Multiforme: A review of where we have been and where we are going", Expert Opin. Investig. Drugs 2009, vol. 18, No. 8; pp. 1061-1083.
Arrowsmith, J. et al., "Antitumor Imidazotetrazines. 41. Conjugation of the Antitumor Agents Mitozolomide and Temozolomide to Peptides and Lexitropsins Bearing DNA Major and Minor Groove-Binding Structural Motifs", J. Med. Chem. 2002, vol. 45; pp. 5458-5470.
Arrowsmith, J. et al., "Antitumour Imidazotetrazines. Part 39. Synthesis of bis(imidazotetrazine)s with saturated spacer groups.", J. Chem. Soc. Perkin Trans. 2000, vol. 1; pp. 4432-4438.
Berrocal, A. et al., "Extended-schedule dose-dense temozolomide in refractory gliomas", J. Neurooncol (2010) vol. 96; pp. 417-422.
Dong, J. et al., "Local delivery of slow-releasing temozolomide microspheres inhibits intracranial xenograft glioma growth", J. Cancer Res Clin Oncol., 2012; vol. 138; pp. 2079-2084.
Fang, C. et al., "Temozolomide Nanoparticles for Targeted Glioblastoma Therapy", ACS Applied Materials & Interfaces, 2015, vol. 7; pp. 6674-6682.
Fourniols, T. et al., "Temozolomide-loaded photopolymerizable PEG-DMA-based hydrogel for the treatment of glioblastoma", Journal of Controlled Release, vol. 210; 2015; pp. 95-104.
Fox, M.E., et al., "Soluble Polymer Carriers for the Treatment of Cancer: The Importance of Molecular Architecture", Accounts of Chemical Research, vol. 42, No. 8, 2009; pp. 1141-1151.
Jauch, T. et al., "Re-challenge with temozolomide (TMZ) at recurrence in high-grade gliomas (HGG)", Journal of Clinical Oncology 25, No. 18_suppl; Jun. 2007; DOI: 10.1200/jco.2007.25.18_suppl. 2034; p. 2034.
Kim, S-S, et al., "Encapsulation of temozolomide in a tumor-targeting nanocomplex enhances anti-cancer efficacy and reduces toxicity in a mouse model of glioblastoma", Cancer Letters, vol. 369, 2015; pp. 250-258.
Larson, N. et al., "Polymeric Conjugates for Drug Delivery", Chemistry of Materials, 2012, vol. 24; pp. 840-853.

(Continued)

*Primary Examiner* — Shobha Kantamneni
(74) *Attorney, Agent, or Firm* — Cantor Colburn LLP

(57) ABSTRACT

A temozolomide compound according to formula (I)

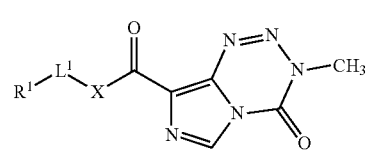

is described, wherein $R^1$, $L^1$, and X are defined herein. The temozolomide compound can be used to prepare polymers comprising temozolomide. Additionally, the polymers comprising temozolomide can be particularly useful in the treatment of certain diseases.

2 Claims, 5 Drawing Sheets

(56) References Cited

OTHER PUBLICATIONS

Liu, D., et al.,"Synthesis and Antitumor Activity of 3-Methyl-4-oxo-3, 4-dihydroimidazo [5,1-d][1,2,3,5]tetrazine-8-carboxylates and -carboxamides", Molecules, 2010, vol. 15; pp. 9427-9436.
Maeda, H., et al., "The EPR Effect for macromolecular drug delivery to solid tumors: Improvement of tumor uptake, lowering of systemic toxicity, and distinct tumor imaging in vivo", Advanced Drug Delivery Reviews, vol. 65, 2013; pp. 71-79.
Mcrae Page, S. et al., "Efficacy of PolyMPC-DOX Prodrugs in 4T1 Tumor-Bearing Mice", Molecular Pharmaceutics, 2014, vol. 11; pp. 1715-1720.
Newlands, E.S. et al., "Temozolomide: a review of its discovery, chemical properties, pre-clinical development and clinical trials", Cancer Treatment Reviews, 1997, vol. 23; pp. 35-61.
Omuro, A. et al., "Glioblastoma and Other Malignant Gliomas", JAMA, 2013, vol. 310, No. 17; pp. 1842-1850.
Ostrom, Q. et al., "CBTRUS Statistical Report: Primary Brain and Central Nervous System Tumors Diagnosed in the United States in 2008-2012", Neuro-Oncology, vol. 17, 2015; pp. iv1-iv62.
Patil, R. et al.,"Temozolomide Delivery to Tumor Cells by a Multifunctional Nano Vehicle Based on Poly(b-L-malic acid)", Pharm. Res., 2010, vol. 27; pp. 2317-2329.
Rottenberg, D.A. et al., "In Vivo Measurement of Regional Brain Tissue pH Using Positron Emission Tomography", Annals of Neurology, 1984, vol. 15; pp. S98-S102.
Skinner, M. et al.,"Versatile Synthesis of Polymer-Temozolomide Conjugates", ACS Macro Letters, vol. 6, 2017; pp. 215-218.
Stevens, M. et al.,"Antitumor Activity and Pharmacokinetics in Mice of 8-Carbamoyl-3-methyl-imidazo[5,1-d]-1,2,3,5-tetrazin-4 (3H)-one(CCRG81045; M&B39831), a Novel Drug with Potential as and Alternative to Dacarbazine1", Cancer Research, vol. 47, 1987; pp. 5846-5852.
Tolcher, A.W. et al., "Marked inactivation of 06-alkylguanine-DNA alkltransferase activity with protracted temozolomide schedules", British Journal of Cancer, 2003, vol. 88, pp. 1004-1011.
Wen, P.Y. et al., "Malignant Gliomas in Adults", The New England Journal of Medicine, 2008, vol. 359; pp. 492-507; Corrections: p. 877.
Wick, A. et al., "Efficacy and Tolerability of Temozolomide in an Alternating Weekly Regimen in Patients With Recurrent Glioma", Journal of Clinical Oncology, vol. 25, No. 22, 2007; pp. 3357-3361.
Wick, W. et al., "One week on/One week off: A novel active regimen of temozolomide for recurrent glioblastoma", Neurology, 2004, vol. 62; pp. 2113-2115.
Wong, K.E. et al., "Evaluation of PolyMPC-Dox Prodrugs in a Human Ovarian Tumor Model", Molecular Pharmaceutics, 2016, vol. 13; pp. 1679-1687.
Zhang, J. et al., "Temozolomide: Mechanisms of Action, Repair and Resistance", Current Molecular Pharmacology, 2012, vol. 5; pp. 102-114.

* cited by examiner

TEMOZOLOMIDE COMPOUNDS, POLYMERS PREPARED THEREFROM, AND METHOD OF TREATING A DISEASE

CROSS REFERENCE TO RELATED APPLICATIONS

This application is a continuing application of U.S. application Ser. No. 15/709,862, filed Sep. 20, 2017, which claims the benefit of U.S. Provisional Application No. 62/398,078, filed Sep. 22, 2016, each of which are incorporated by reference herein in their entirety.

STATEMENT REGARDING FEDERALLY SPONSORED RESEARCH & DEVELOPMENT

This invention was made with government support under award number DMR-0820506 awarded by the National Science Foundation Materials Research Science & Engineering Center (MRSEC) on Polymers and under award number R21 CA167674 awarded by the National Institutes of Health. The government has certain rights in the invention.

BACKGROUND

Temozolomide (TMZ) is a first-line chemotherapeutic indicated for treating patients diagnosed with glioblastoma. Administered orally, TMZ is a lipophilic, acid-stable DNA alkylating agent that efficiently crosses the blood-brain barrier and presents mild side effects. See, e.g., Adamson, C.; Kanu, O. O.; Mehta, A. I.; Di, C.; Lin, N.; Mattox, A. K.; Bigner, D. D. Glioblastoma Multiforme: A Review of Where We Have Been and Where We Are Going. *Expert Opin. Investig. Drugs* 2009, 18, 1061-1083. Serving as a small molecule prodrug, TMZ hydrolyzes spontaneously at physiologic pH liberating methyldiazonium cations that elicit antitumor activity by methylation of guanine and adenine nucleobases. See, e.g., Zhang, J.; Stevens, M. F. G.; Bradshaw, T. D. Temozolomide: Mechanisms of Action, Repair and Resistance. *Curr. Mol. Pharmacol.* 2012, 5, 102-114; Newlands, E. S.; Stevens, M. F. G.; Wedge, S. R.; Wheelhouse, R. T.; Brock, C. Temozolomide: A Review of Its Discovery, Chemical Properties, Pre-Clinical Development and Clinical Trials. *Cancer Treat. Rev.* 1997, 23, 35-61. Owing to the slightly alkaline microenvironment of brain tumors (see, e.g., Rottenberg, D. A.; Ginos, J. Z.; Kearfoot, K. J.; Junck, L.; Bigner, D. D. In Vivo Measurement of Regional Brain Tissue pH Using Positron Emission Tomography. *Ann. Neurol.* 1984, 15, S98-102) this pH-induced mechanism of action confers selective cytotoxicity for malignant versus healthy brain tissue (see, e.g., Zhang, J.; Stevens, M. F. G.; Bradshaw, T. D. Temozolomide: Mechanisms of Action, Repair and Resistance. Curr. *Mol. Pharmacol.* 2012, 5, 102-114) resulting in limited off-target toxicity. Unfortunately, in vivo decomposition and clearance of TMZ is rapid, and frequent dosing is required to retain antitumor activity. See, e.g., Stevens, M. F. G.; Hickman, J. A.; Langdon, S. P.; Chubb, D.; Vickers, L.; Stone, R.; Baig, G.; Goddard, C.; Gibson, N. W.; Slack, J. A.; Newton, C.; Lunt, E.; Fizames, C.; Lavelle, F. Antitumor Imidazo[5,1-d]-1,2,3,5-Tetrazin-4(3H)-One (CCRG 81045: M & B39831), a Novel Drug with Potential as an Alternative to Dacarbazine. *Cancer Res.* 1987, 47, 5846-5852. Moreover, efficacy is often hampered by chemoresistance primarily induced by $O^6$-methylguanine-DNA methyltransferase (MGMT), a native enzyme that repairs damaged DNA following methylation. See, e.g., Newlands, E. S.; Stevens, M. F. G.; Wedge, S. R.; Wheelhouse, R. T.; Brock, C. Temozolomide: A Review of Its Discovery, Chemical Properties, Pre-Clinical Development and Clinical Trials. *Cancer Treat. Rev.* 1997, 23, 35-61. Clinical examination has shown that MGMT activity in glioblastoma tumors can be depleted by sustained TMZ exposure (see, e.g., Tolcher, A. W.; Gerson, S. L.; Denis, L.; Geyer, C.; Hammond, L A.; Patnaik, A.; Goetz, A. D.; Schwartz, G.; Edwards, T.; Reyderman, L.; Statkevich, P.; Cutler, D. L.; Rowinsky, E. K. Marked Inactivation of $O^6$-Alkylguanine-DNA Alkyltransferase Activity with Protracted Temozolomide Schedules. *Br. J. Cancer* 2003, 88, 1004-1011), and that recurrent glioblastoma treated with protracted dosing schedules can improve tumor response. See, e.g., Wick, W.; Steinbach, J. P.; Kuker, W. M.; Dichgan, J.; Bamberg, M.; Weller, M. One week On/One Week Off: a Novel Active Regimen of Temozolomide for Recurrent Glioblastoma. Neurology 2004, 62, 2113-2115; Jauch, T.; Hau, P.; Bogdahn, U. Re-challenge with Temozolomide (TMZ) at Recurrence in High-Grade Gliomas (HGG). *J. Clin. Onocol.* 2007, 25, 2034; Wick, A.; Felsberg, J.; Steinbach, J. P.; Herrlinger, U.; Platten, M.; Blaschke, B.; Meyermann, R.; Reifenberger, G.; Weller, M.; Wick, W. Efficacy and Tolerability of Temozolomide in an Alternating Weekly Regimen in Patients with Recurrent Glioma. *J. Clin. Oncol.* 2007, 25, 3357-3361; Berrocal, A.; Perez Segura, P.; Gil, M.; Balanfa, C.; Garcia Lopez, J.; Yaya, R.; Rodriguez, J.; Reynes, G.; Gallego, O.; Iglesias, L.; GENOM Cooperative Group. Extended-Schedule Dose-Dense Temozolomide in Refractory Gliomas. *J. Neurooncol.* 2010, 96, 417-422. As these alternative regimens can increase occurrence of dose-limiting hematoxicity, an alternative therapeutic modality that extends TMZ circulation and masks drug-associated toxicity is desired.

Polymer-drug conjugation is effective for augmenting the antitumor efficacy of many small molecule chemotherapeutics, affording water-soluble prodrugs with improved pharmacokinetic behavior. See, e.g., Larson, N.; Ghandehari, H. Polymeric Conjugates for Drug Delivery. *Chem. Mater.* 2012, 24, 840-853; Fox, M. E.; Szoka, F. C.; Fréchet, J. M. J. Soluble Polymer Carriers for the Treatment of Cancer: The Importance of Molecular Architecture. *Acc. Chem. Res.* 2009, 42, 1141-1151. As a result of the leaky vasculature and poor lymphatic drainage of solid tumors, polymer therapeutic accumulation in malignant tissue is enhanced, leading to potentiated antitumor activity and reduced off-target toxicity. See, e.g., Maeda, H.; Nakamura, H.; Fang, J. The EPR Effect for Macromolecular Drug Delivery to Solid Tumors: Improvement of Tumor Uptake, Lowering of Systemic Toxicity, and Distinct Tumor Imaging In Vivo. *Adv. Drug Delivery Rev.* 2013, 65, 71-79.

Various delivery strategies have been explored for improving TMZ therapy, including encapsulation in nanoparticles and liposomes for systemic administration, as well as entrapment in hydrogels, degradable matrices, and microspheres for localized treatments (see, e.g., Fang, C.; Wang, K.; Stephen, Z. R.; Mu, Q.; Kievit, F. M.; Chiu, D. T.; Press, O. W.; Zhang, M. Temozolomide Nanoparticles for Targeted Glioblastoma Therapy. *ACS Appl. Mater. Interfaces* 2015, 7, 6674-6682; Kim, S-S.; Rait, A.; Kim, E.; DeMarco, J.; Pirollo, K. F.; Chang, E. H. Encapsulation of Temozolomide in a Tumor-Targeting Nanocomplex Enhances Anti-Cancer Efficacy and Reduces Toxicity in a Mouse Model of Glioblastoma. *Cancer Lett.* 2015, 369, 250-258; Dong, J.; Zhou, G.; Tang, D.; Chen, Y.; Cui, B.; Dai, X.; Zhang, J.; Lan, Q.; Huang, Q. Local Delivery of Slow-Releasing Temozolomide Microspheres Inhibits Intracranial Xenograft Glioma Growth. *J. Cancer Res. Clin. Oncol.* 2012, 138, 2079-2084; Fourniols, T.; Randolph, L. D.; Staub, A.; Vanvarenberg, K.; Leprince, J. G.; Préat, V.; des Rieux, A.; Danhier, F. Temozolomide-Loaded Photopolymerizable PEG-DMA-Based Hydrogel for the Treatment of Glioblastoma. *J. Controlled Release* 2015, 210, 95-104). To date, only one example of a polymer-TMZ therapeutic, prepared using metabolically-derived poly(β-L-malic acid), has been reported. See, e.g., Patil, R.; Portilla-Arias, J.; Ding, H.; Inoue, S.; Konda, B.; Hu, J.; Wawrowsky, K. A.; Shin, P. K.; Black, K. L.; Holler, E.; Ljubimova, J. Y. Temozolomide Delivery to Tumor Cells by a Multifunctional Nano Vehicle Based on Poly(β-ι-malic acid). *Pharm. Res.* 2010, 27, 2317-2329. While this conjugate demonstrated in vitro activity against glioblastoma tumor cells, including a naturally chemoresistant cell line, chemical and physical characterization of the polymer prodrug was limited, and the synthetic strategy employed was not suitable for preparing well-defined structures with tunable drug content.

Glioblastoma is a cerebral neoplasm that represents the most prolific malignant central nervous system tumor diagnosed in the United States, with nearly 11,000 new cases presented annually. See, e.g., Ostrom, Q. T.; Gittleman, H.; Fulop, J.; Liu, M.; Blanda, R.; Kromer, C.; Wolinsky, Y.; Kruchko, C.; Barnholtz-Sloan, J. S. CBTRUS Statistical Report: Brain and Central Nervous System Tumors Diagnosed in the United States in 2008-2012. *Neuro Oncol.* 2015, 17, iv1-iv62. Characterized by substantial histologic and genetic heterogeneity, glioblastoma is an infiltrative astrocytoma with dismal patient prognosis. Even with early detection, median survival of only 12 to 15 months is expected following treatment. See, e.g., Omura, A.; DeAngelis, L. M. Glioblastoma and Other Malignant Gliomas. *JAMA* 2013, 310, 1842-1850; Wen, P. Y.; Kesari, S. Malignant Gliomas in Adults. *N. Engl. J. Med.* 2008, 359, 492-507. Standard of care for patients with newly diagnosed glioblastoma includes surgical debulking to resect maximal solid tumor tissue, followed by chemoradiotherapy and adjuvant chemotherapy with TMZ. Though therapeutic intervention can temporarily arrest disease progression, recurrence is generally inevitable.

Accordingly, there remains a continuing need for improved delivery systems for TMZ (e.g., polymer delivery systems), particularly for the treatment of cancer (e.g., glioblastoma).

BRIEF SUMMARY

One embodiment is a temozolomide compound of structure (I)

(I)

wherein X is —O— or —NR$^a$—, wherein R$^a$ is hydrogen or a $C_{1-6}$ alkyl group; L$^1$ is a divalent $C_{1-12}$ alkylene group, di($C_{2-12}$) alkylene disulfide group, $C_{2-12}$ alkylene ester group, $C_{6-20}$ arylene group, $C_{1-20}$ alkylene oxide group, or $C_{1-12}$ alkylene sulfide group; n is 0 or 1; and R$^1$ is a group of the formula H$_2$C=C(R$^b$)—(C=O)—W—, wherein R$^b$ is methyl, hydrogen, fluoro, cyano, or trifluoromethyl, and W is —O— or —NH—; an alkenyl group; an alkynyl group; an aldehyde group; a ketone group; a thiol group; a pentafluorophenyl group, a pyridyl disulfide group, a zwitterionic group, a glutathione group, a thiamine group, or a poly(ethylene glycol) group.

Another embodiment is a polymer comprising repeating units comprising temozolomide derived from the temozolomide compound, and optionally, repeating units of formula (II), formula (III), or a combination thereof

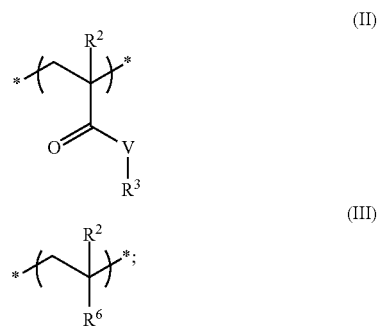

wherein in each occurrence of the repeating units of formula (II) R$^2$ is a hydrogen or a $C_{1-6}$ alkyl group; V is —O— or —NH—; and R$^3$ is a zwitterionic group, a poly($C_{1-6}$ alkylene oxide) group, a hydroxy-substituted $C_{1-6}$ alkyl group, or a $C_{1-12}$ alkyl group; and wherein in each occurrence of the repeating units of formula (III) R$^2$ is a hydrogen or a $C_{1-6}$ alkyl group; and R$^6$ is a $C_{6-20}$ aryl group.

Another embodiment is a poly(ethylene glycol)-temozolomide conjugate comprising a poly(ethylene glycol) having at least two chain ends conjugated to a temozolomide compound.

Another embodiment is a method of treating a disease, the method comprising administering a therapeutically effective amount of a composition comprising the polymer.

These and other embodiments are described in detail below.

DETAILED DESCRIPTION

Figure 1:
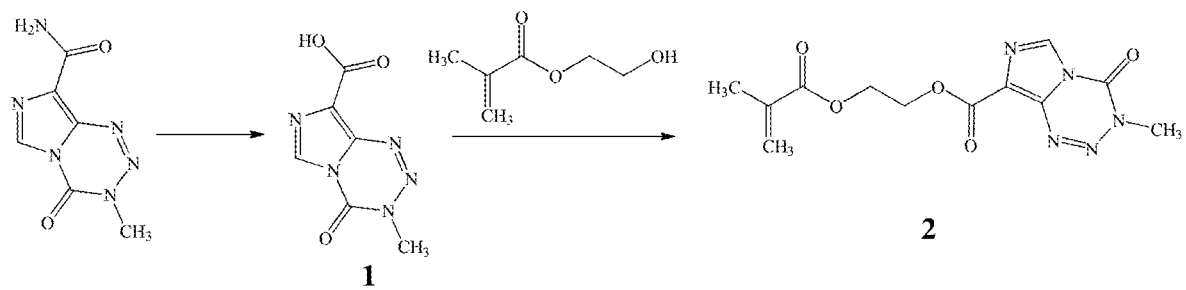
FIG. 1 is a chemical scheme depicting the synthesis of TMZ-methacrylate (shown as compound 2).

The present inventors have discovered new synthetic compositions of temozolomide (TMZ). Through the use of new functional derivatives of TMZ, homo- and copolymers comprising TMZ can be prepared, including both water-soluble TMZ-containing polymers, as well as water-insoluble formulations. The TMZ-containing polymers described herein are thought to be particularly useful in the treatment of certain cancers. The TMZ-containing polymers described herein can advantageously be prepared as injectable TMZ-containing formulations for systemic treatment of such diseases, or as implantable TMZ-containing formulations. Without wishing to be bound by theory, it is believed that the increased size of the TMZ-containing polymers relative to TMZ itself can extend the in vivo circulation time, reduce treatment frequency, and provide opportunities for increased drug accumulation in tumors through the enhanced permeability and retention effect (e.g., when used as an injectable formulation). Additionally, the TMZ-containing polymers described herein can potentially assemble in solution resulting from hydrophobic drug interactions, which can serve to enhance TMZ stability and lifetime in the bloodstream. Small molecule, water-soluble TMZ derivatives are also discussed.

Accordingly, an aspect of the present disclosure is a temozolomide compound. In some embodiments, the temozolomide compounds of the present disclosure advantageously include a functional group that can be used for subsequent conjugation of the temozolomide compound to, for example, a polymer carrier, or other drug delivery platform. In other embodiments, the temozolomide compounds of the present disclosure can include a water-solubilizing group which can provide temozolomide as a small molecule (i.e., not conjugated to a polymer scaffold) in a water soluble form. In particular, the temozolomide compound has the structure according to formula (I)

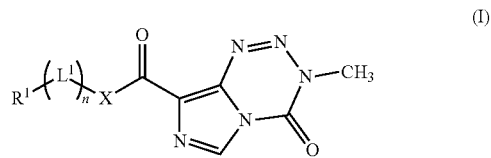

wherein X is —O— or —NR$^a$—, wherein R$^a$ is hydrogen or a C$_{1-6}$ alkyl group. In some embodiments, X is —O—. In some embodiments, X is —NR$^a$—, wherein R$^a$ is preferably hydrogen (i.e., X is —NH—). L$^1$ is a divalent C$_{1-12}$ alkylene group, di(C$_{2-12}$ alkylene) disulfide group (e.g., —(C$_{2-12}$ alkylene)-S—S—(C$_{2-12}$ alkylene)-), C$_{2-12}$ alkylene ester group, C$_{6-20}$ arylene group, C$_{1-20}$ alkylene oxide group, or C$_{1-12}$ alkylene sulfide group. In some embodiments, L$^1$ can be a divalent C$_{1-12}$ alkylene group, di(C$_{2-12}$ alkylene) disulfide group (e.g., —(C$_{2-12}$ alkylene)-S—S—(C$_{2-12}$ alkylene)-), C$_{2-12}$ alkylene ester group, C$_{6-20}$ arylene group, or C$_{1-20}$ alkylene oxide group. In some embodiments, L$^1$ is preferably a divalent C$_{1-12}$ alkylene group, di(C$_{2-12}$ alkylene) disulfide group, or C$_{1-20}$ alkylene oxide group, more preferably a divalent C$_{1-12}$ alkylene group or di(C$_{2-12}$ alkylene) disulfide group, even more preferably a divalent C$_{1-12}$ alkylene group. In some embodiments, L$^1$ is a C$_{1-6}$ alkylene group. In some embodiments, L$^1$ is a C$_{2-6}$ alkylene group. Further in formula (I), n can be 0 or 1.

R$^1$ in formula (I) is a group of the formula H$_2$C=C(R$^b$)—(C=O)—W—, wherein R$^b$ is methyl, hydrogen, fluoro, cyano, or trifluoromethyl, and W is —O— or —NH—; an alkenyl group; an alkynyl group; an aldehyde group; a ketone group, or a thiol group. In some embodiments, R$^1$ is a group of the formula H$_2$C=C(R$^b$)—(C=O)—O—, wherein R$^b$ is methyl, hydrogen, fluoro, cyano, or trifluoromethyl. In some embodiments, R$^b$ is a hydrogen, and R$^1$ is an acrylate group. In some embodiment, R$^b$ is a methyl group, and R$^1$ is a methacrylate group. In some embodiments, R$^1$ is a group of the formula H$_2$C=C(R$^b$)—(C=O)—NH—, where R$^b$ is preferably a methyl group, and R$^1$ is a methacrylamide group. In some embodiments, R$^1$ is a group of the formula H$_2$C=C(R$^b$)—(C=O)—NH—, where R$^b$ is preferably a hydrogen, and R$^1$ is an acrylamide group. In some embodiments, R$^1$ is an alkenyl group (e.g., a vinyl group (H$_2$C=CH—), an allyl group (H$_2$C=CH—CH$_2$—), a vinyl ether group (H$_2$C=CH—O—), a styryl group (H$_2$C=CH—(C$_6$H$_4$)—), and the like). In some embodiments, R$^1$ is an alkynyl group (e.g., an ethynyl group (HC≡C—), a propargyl group (HC≡C—CH$_2$—), a propargyl ether group (HC≡C—CH$_2$—O—), and the like). In some embodiments, R$^1$ is an aldehyde group (e.g., H(C=O)—, a benzaldehyde group (H(C=O)—(C$_6$H$_4$)—, and the like). In some embodiments, R$^1$ is a ketone group (e.g., (C$_{1-6}$ alkyl)-(C=O)—). In some embodiments, R$^1$ is a thiol group, for example, a thiol group of the formula HS—. In some embodiments, R$^1$ is a pentafluorophenyl group. In some embodiments, R$^1$ is a zwitterionic group (e.g., of the formula A-B-C-, wherein A is a center of permanent positive charge or a center of permanent negative charge; B is a divalent group comprising a C$_{1-12}$ alkylene group, a C$_{6-30}$ arylene or heteroarylene group, or an alkylene oxide group; and C is a center of permanent positive charge or a center of permanent negative charge, provided that the zwitterionic group has an overall net charge of zero). In some embodiments, R$^1$ is a pyridyl disulfide group. In some embodiments, R¹ is a glutathione group. In some embodiments, R¹ is a thiamine group. In some embodiments, R¹ is a poly(ethylene glycol) group.

In some embodiments, R¹ is of the formula

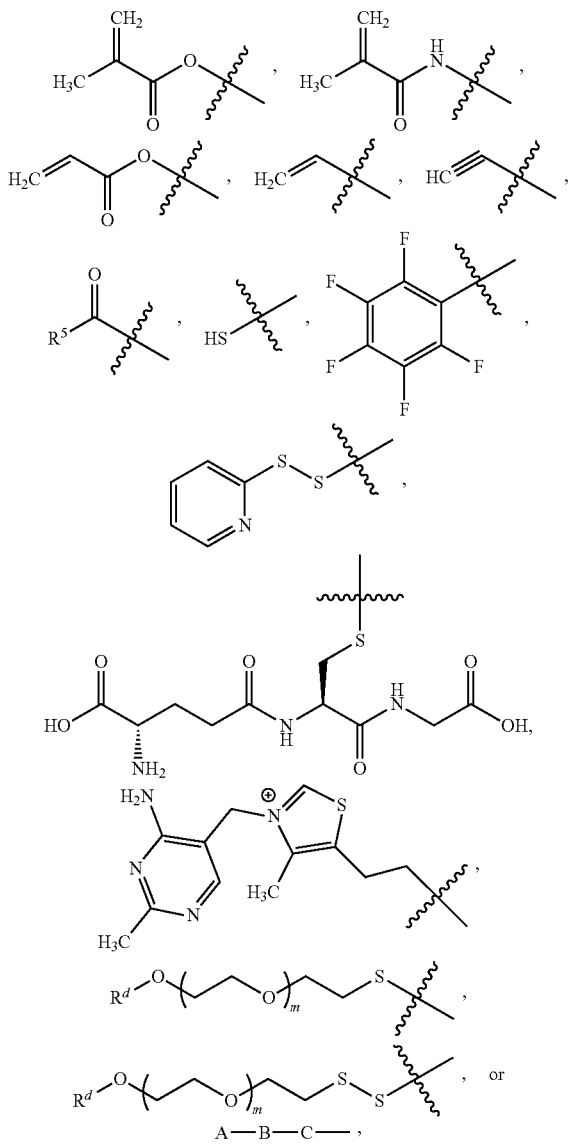

wherein in the above formulas, R⁵ is hydrogen or a $C_{1-6}$ alkyl group, $R^d$ is hydrogen or a $C_{1-6}$ alkyl group, m is an integer from greater than 1 to 900; A is a center of permanent positive charge or a center of permanent negative charge; B is a divalent group comprising a $C_{1-12}$ alkylene group, a $C_{6-30}$ arylene or heteroarylene group, or an alkylene oxide group; C is a center of permanent positive charge or a center of permanent negative charge, provided that the zwitterionic group has an overall net charge of zero; and the curved line indicates the point of attachment of the R¹ group to the rest of the temozolomide compound (e.g., via linking group L¹).

In some embodiments, when R¹ is a group of the formula $H_2C=C(R^b)-(C=O)-O-$, wherein $R^b$ is methyl, hydrogen, fluoro, cyano, or trifluoromethyl; an aldehyde group; or a thiol group, X is —O—. In some embodiments, when R¹ is an alkenyl group or an alkynyl group, X is —NH—.

In an embodiment, the temozolomide compound is of formula (I) and X is —O—; n is 1; L¹ is a divalent $C_{1-6}$ alkylene group; and R¹ is a methacrylate group. In some embodiments, L¹ is a divalent $C_{2-6}$ alkylene group, preferably a $C_2$ alkylene group. For example, the temozolomide compound can be of the formula

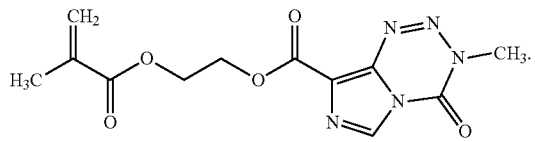 [SMILES: C=C(C)C(=O)OCCOC(=O)c1ncn2c(=O)n(C)nnc12]

In an embodiment, the temozolomide compound is of formula (I) and X is —O—; n is 1; L¹ is a divalent $C_{1-6}$ alkylene group; and R¹ is an acrylate group. In some embodiments, L¹ is a divalent $C_{24}$ alkylene group, preferably a $C_2$ alkylene group. For example, the temozolomide compound can be of the formula

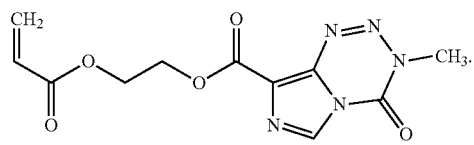 [SMILES: C=CC(=O)OCCOC(=O)c1ncn2c(=O)n(C)nnc12]

In an embodiment, the temozolomide compound is of formula (I) and X is —O—; n is 1; L¹ is a divalent $C_{1-6}$ alkylene group; and R¹ is a methacrylamide group. In some embodiments, L¹ is a divalent $C_{2-6}$ alkylene group, preferably a $C_2$ alkylene group. For example, the temozolomide compound can be of the formula

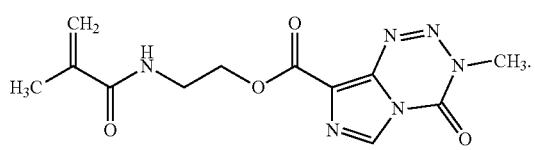 [SMILES: C=C(C)C(=O)NCCOC(=O)c1ncn2c(=O)n(C)nnc12]

In an embodiment, the temozolomide compound is of formula (I) and X is —NH—; n is 1; L¹ is a divalent $C_{1-6}$ alkylene group; and R¹ is a methacrylamide group. In some embodiments, L¹ is a divalent $C_{2-6}$ alkylene group, preferably a $C_2$ alkylene group. For example, the temozolomide compound can be of the formula

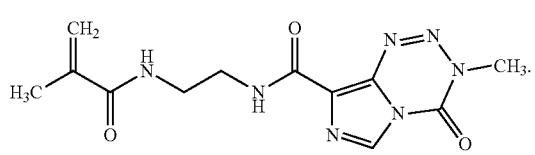 [SMILES: C=C(C)C(=O)NCCNC(=O)c1ncn2c(=O)n(C)nnc12]

In an embodiment, the temozolomide compound is of formula (I) and X is —NH—; n is 1; L¹ is a divalent $C_{1-6}$ alkylene group; and R¹ is an acrylamide group. In some embodiments, L¹ is a divalent $C_{2-6}$ alkylene group, preferably a $C_2$ alkylene group. For example, the temozolomide compound can be of the formula

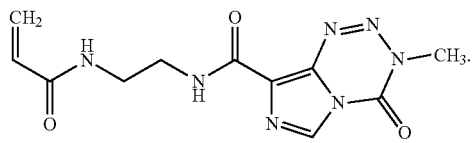 [SMILES: C=CC(=O)NCCNC(=O)c1ncn2c(=O)n(C)nnc12]

In an embodiment, the temozolomide compound is of formula (I) and X is —O—; n is 1; $L^1$ is a divalent di($C_{1-6}$ alkylene) disulfide group; and $R^1$ is a methacrylate group. In some embodiments, $L^1$ is a divalent di($C_{2-6}$ alkylene) disulfide group, preferably a divalent di($C_2$ alkylene) disulfide group (e.g., —($C_2H_4$)—S—S—($C_2H_4$)—). For example, the temozolomide compound can be of the formula

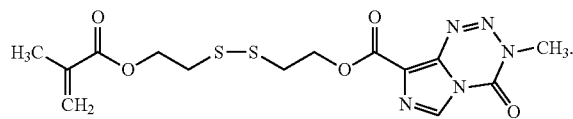 [SMILES: C=C(C)C(=O)OCCSSCCOC(=O)c1ncn2c(=O)n(C)nnc12]

In an embodiment, the temozolomide compound is of formula (I) and X is —O—; n is 1; $L^1$ is a divalent $C_{1-6}$ alkylene group; and $R^1$ is an aldehyde group or a ketone group. In some embodiments, $L^1$ is a divalent $C_{2-6}$ alkylene group, preferably a $C_2$ alkylene group. In some embodiments, when $R^1$ is a ketone group, $R^5$ can be a methyl group or an ethyl group, preferably a methyl group. For example, the temozolomide compound can be of the formula

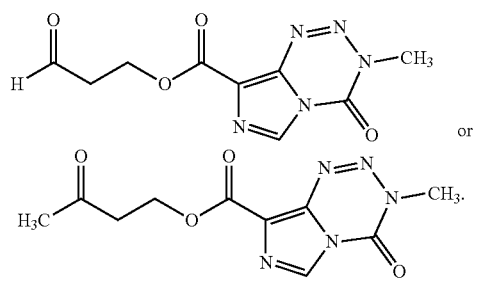

In an embodiment, the temozolomide compound is of formula (I) and X is —O—; n is 1; $L^1$ is a divalent $C_{1-6}$ alkylene group; and $R^1$ is a thiol group. In some embodiments, $L^1$ is a divalent $C_{2-6}$ alkylene group, preferably a $C_3$ alkylene group. For example, the temozolomide compound can be of the formula

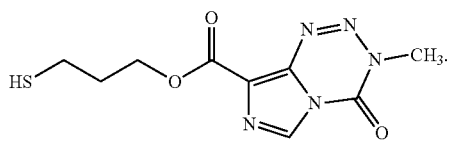 [SMILES: Cn1nnc2c(C(=O)OCCCS)ncn2c1=O]

In an embodiment, the temozolomide compound is of formula (I) and X is —NH—; n is 1; $L^1$ is a divalent $C_{1-6}$ alkylene group; and $R^1$ is a vinyl group. In some embodiments, $L^1$ is a divalent $C_{1-3}$ alkylene group, preferably a $C_1$ alkylene (e.g., a methylene) group. For example, the temozolomide compound can be of the formula In an embodiment, the temozolomide compound is of formula (I) and X is —NH—; n is 1; $L^1$ is a divalent $C_{1-6}$ alkylene group; and $R^1$ is an ethynyl group. In some embodiments, $L^1$ is a divalent $C_{1-3}$ alkylene group, preferably a $C_1$ alkylene (e.g., a methylene) group. For example, the temozolomide compound can be of the formula In an embodiment, the temozolomide compound is of formula (I) and X is —O—; n is 0; and $R^1$ is a pentafluorophenyl group. For example, the temozolomide compound can be of the formula In an embodiment, the temozolomide compound is of formula (I) and X is —O—; n is 1; $L^1$ is a divalent $C_{1-6}$ alkylene group; and $R^1$ is a pyridyl disulfide group. In some embodiments, $L^1$ is a divalent $C_{1-3}$ alkylene, preferably a $C_2$ alkylene (e.g., an ethylene) group. For example, the temozolomide compound can be of the formula In an embodiment, the temozolomide compound is of formula (I) and X is —O— or —NH—; n is 1; $L^1$ is a divalent $C_{1-12}$ alkylene sulfide group or a divalent $C_{1-6}$ alkylene group; and $R^1$ is a glutathione group. For example, the temozolomide compound can be of the formula

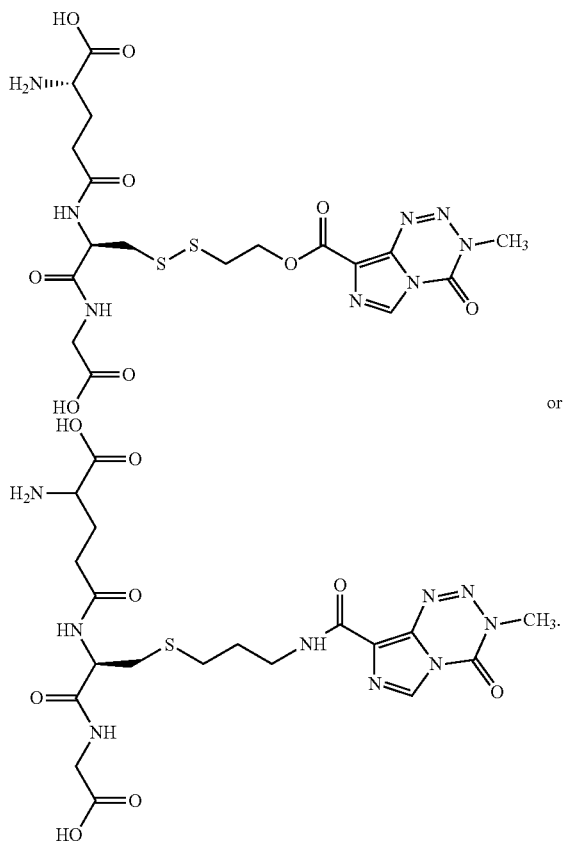

In an embodiment, the temozolomide compound is of formula (I) and X is —NH— or —O—; n is 1; $L^1$ is a divalent $C_{1-12}$ alkylene sulfide group; and $R^1$ is a thiamine group. For example, the temozolomide compound can be of the formula

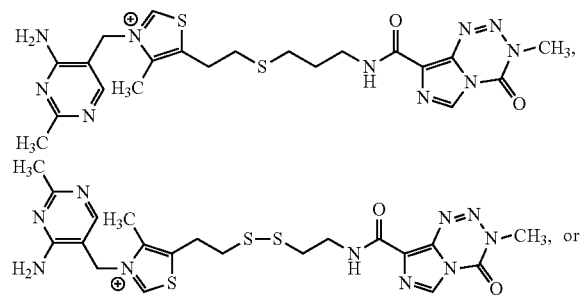

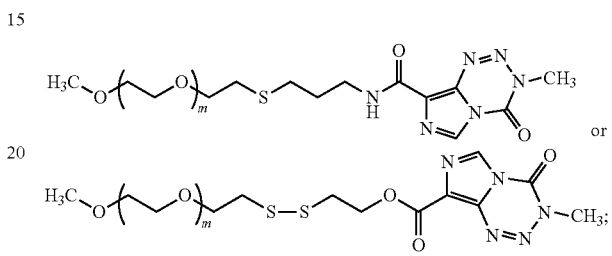

In an embodiment, the temozolomide compound is of formula (I) and X is —O— or —NH—; n is 1; $L^1$ is a di($C_{2-12}$ alkylene) disulfide group or $C_{1-12}$ alkylene sulfide group; and $R^1$ is a poly(ethylene glycol) group. For example, the temozolomide compound can be of the formula

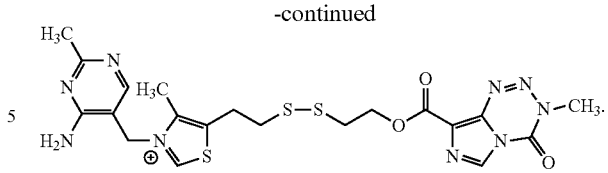

wherein m is an integer from greater than 1 to 900, or 1 to 500, or 1 to 250, or 1 to 100, or 1 to 50.

In an embodiment, the temozolomide compound is of formula (I) and X is —O— or —NH—; n is 1; $L^1$ is a divalent di($C_{2-12}$ alkylene) disulfide group, $C_{2-12}$ alkylene ester group, $C_{6-20}$ arylene group, $C_{1-20}$ alkylene oxide group, or $C_{1-12}$ alkylene sulfide group; and $R^1$ is a phosphorylcholine zwitterionic group having the structure A-B-C-, wherein A is an ammonium group of the formula —N($R^7$)$_3$, wherein $R^7$ is a $C_{1-6}$ alkyl group; B is a divalent $C_{1-6}$ alkylene group; and C is a divalent phosphate group. In another embodiment, X is —O— or —NH—; n is 1; $L^1$ is a divalent $C_{1-6}$ alkylene group; and $R^1$ is a sulfobetaine zwitterionic group having the structure A-B-C-$L^2$-, wherein A is a sulfonate group; B is a divalent $C_{1-6}$ alkylene group; C is a divalent ammonium group; and $L^2$ is a divalent $C_{1-6}$ alkylene group; wherein $L^2$ of the zwitterionic group is covalently bound to $L^1$ through a thioether bond or a disulfide bond. In yet another embodiment, X is —O— or —NH—; n is 1; $L^1$ is a divalent $C_{1-6}$ alkylene group; and $R^1$ is a carboxybetaine zwitterionic group having the structure A-B-C-$L^2$-, wherein A is a carboxylate group; B is a divalent $C_{1-6}$ alkylene group; C is a divalent ammonium group; and $L^2$ is a divalent $C_{1-6}$ alkylene group; wherein $L^2$ of the zwitterionic group is covalently bound to $L^1$ through a thioether bond or a disulfide bond. For example, the temozolomide can be of the formula

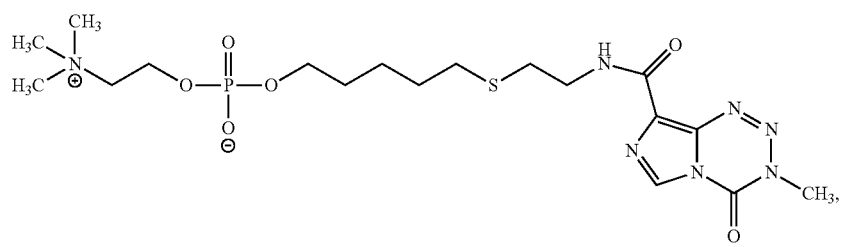

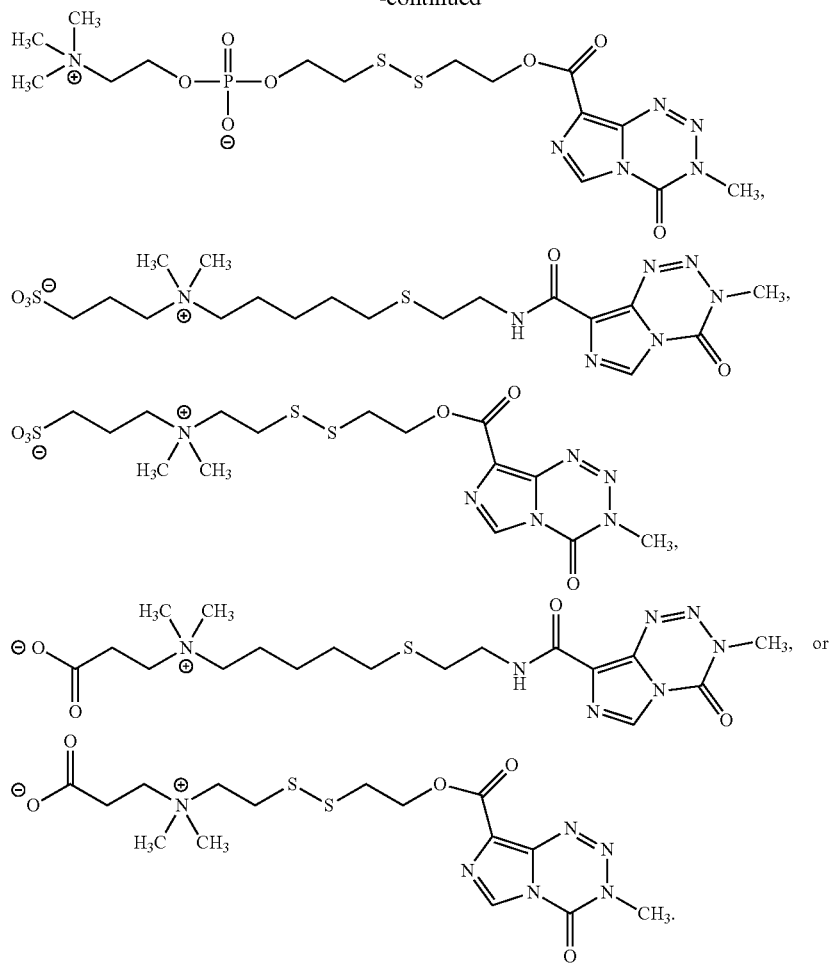

In some embodiments, the $R^1$ group is preferably a functional g cup that enables further functionalization of the temozolomide compound (i.e., conjugation to a polymer scaffold or a water soluble group, as further discussed below, and as demonstrated in the working examples). Thus, $R^1$ can preferably be a group of the formula $H_2C=C(R^b)-(C=O)-W-$, wherein $R^b$ is methyl, hydrogen, fluoro, cyano, or trifluoromethyl, and W is —O— or —NH—; an alkenyl group; an alkynyl group; an aldehyde group; a ketone group; a thiol group, a pentafluorophenyl group, or a pyridyl disulfide group.

Thus, the above-described forms of the temozolomide compound described herein can be particularly useful for conjugation (e.g., covalent attachment) of temozolomide to a drug delivery platform, for example, a polymer carrier. The polymer can be a homopolymer containing repeating units derived from the temozolomide compound, or can be a copolymer containing repeating units derived from the temozolomide compound and other repeating units. The copolymer can be a random copolymer or a block copolymer. The polymer carrier can be water soluble or water insoluble. The solubility of the polymer carrier can be selected depending on the desired method of administration of the temozolomide-containing polymer to a subject (e.g., injectable delivery vs. implantable delivery). In some embodiments, the polymer carrier is preferably water soluble. As used herein, the term "water-soluble" refers to polymers that form a solution in water that is free of insoluble polymer particles. The determination that a solution is free of insoluble polymer particles can be made using conventional light scattering techniques or by passing the solution through a sufficiently fine filter screen capable of capturing insoluble polymer particles. For example, a water soluble polymer can have a water solubility of at least 10 milligrams per milliliter.

Thus, another aspect of the present disclosure is a polymer comprising repeating units comprising temozolomide, wherein the repeating units are derived from the above-described temozolomide compounds. In addition to the repeating units comprising temozolomide derived from the temozolomide compounds described above, the polymer can also optionally comprise repeating units of formula (II), formula (III), or a combination thereof

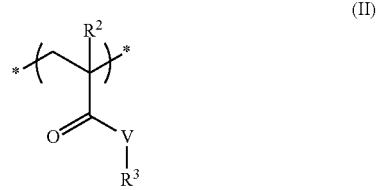

(II)

-continued

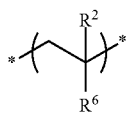
(III)

wherein in each occurrence of the repeating units of formula (II), $R^2$ is independently at each occurrence a hydrogen or a $C_{1-6}$ alkyl group, V is independently at each occurrence —O— or —NH—, and $R^3$ is independently at each occurrence a zwitterionic group, a poly($C_{1-6}$ alkylene oxide) group, a hydroxy-substituted $C_{1-6}$ alkyl group, or a $C_{1-12}$ alkyl group. In some embodiments, $R^2$ is preferably a $C_{1-6}$ alkyl group, more preferably a methyl group. In each occurrence of the repeating units of formula (III), $R^2$ is independently at each occurrence a hydrogen or a $C_{1-6}$ alkyl group, and $R^6$ is independently at each occurrence a substituted or unsubstituted $C_{6-20}$ aryl group, preferably wherein $R^2$ is hydrogen and $R^6$ is a $C_6$ aryl group (i.e., the repeating units according to formula (III) can be styrene repeating units).

In some embodiments, the polymer can be a homopolymer comprising repeating units comprising temozolomide, wherein the repeating units are derived from the above-described temozolomide compounds. The homopolymer can include 100 mole percent of repeating units comprising temozolomide based on the total repeating units of the polymer. In some embodiments, the homopolymer can include less than 10 mole percent, or less than 5 mole percent, or less than 1 mole percent of repeating units other than repeating units comprising temozolomide, based on the total repeating units of the polymer.

In some embodiments, the polymer can be a copolymer comprising repeating units comprising temozolomide and repeating units of formula (II) wherein $R^2$ is a $C_{1-6}$ alkyl group, preferably a methyl group, V is —O—, and $R^3$ is a $C_{1-12}$ alkyl group, preferably a $C_{1-6}$ alkyl group, more preferably a methyl group. In some embodiments, the polymer can be a copolymer comprising repeating units comprising temozolomide and repeating units of formula (III) wherein $R^2$ is a hydrogen and $R^6$ is a substituted or unsubstituted $C_6$ aryl group. The copolymer can comprise 1 to 95 mole percent, or 1 to 90 mole percent, or 1 to 75 mole percent, or 1 to 60 mole percent, or 10 to 50 mole percent of repeating units comprising temozolomide based on the total repeating units of the copolymer. The copolymer can be insoluble in water, for example, the copolymer can have a solubility in water of less than 10 milligrams per milliliter, or less than 5 milligrams per milliliter, or less than 1 milligram per milliliter.

In some embodiments, the polymer can be a copolymer comprising repeating units comprising temozolomide and repeating units of formula (II) wherein $R^2$ is a $C_{1-6}$ alkyl group, preferably a methyl group, V is —O—, and $R^3$ is independently at each occurrence a zwitterionic group, a poly($C_{1-6}$ alkylene oxide) group, or a hydroxy-substituted $C_{1-6}$ alkyl group. The copolymer can comprise 1 to 95 mole percent, or 1 to 90 mole percent, or 1 to 75 mole percent, or 1 to 60 mole percent, or 5 to 55 mole percent, or 10 to 55 mole percent, or 15 to 55 mole percent of repeating units comprising temozolomide. The copolymer can be water soluble, wherein the term water soluble is as defined above.

In some embodiments, the polymer is a copolymer comprising repeating units of formulas (II) wherein $R^3$ is a zwitterionic group. A zwitterionic group can have the structure -$L^2$-A-B-C, wherein $L^2$ is a divalent linking group, A is a center of permanent positive charge or a center of permanent negative charge, B is a divalent group comprising a $C_{1-12}$ alkylene group, a $C_{6-30}$ arylene group, or an alkylene oxide group, and C is a center of permanent negative charge or a center of permanent positive charge, provided that the zwitterion has an overall net charge of zero (i.e., the zwitterion is net neutral). For example, in an embodiment wherein A is a center of permanent positive charge, C is a center of permanent negative charge. For example, in an embodiment wherein A is a center of permanent negative charge, C is a center of permanent positive charge. In some embodiments, a center of permanent positive charge can include a quaternary ammonium group, a phosphonium group, a sulfonium group, and the like. In some embodiments, the center of permanent positive charge is preferably an ammonium group. In some embodiments, a center of permanent negative charge can include a sulfonate group, a phosphonate group, a carboxylate group, a thiolate group, and the like. The linking group $L^2$ is a divalent $C_{1-12}$ alkylene group, $C_{6-20}$ arylene group, or $C_{1-20}$ alkylene oxide group. In some embodiments, $L^2$ is preferably a divalent $C_{1-12}$ alkylene group, more preferably a $C_{1-6}$ alkylene group.

In some embodiments, the zwitterionic group can be a phosphorylcholine group, a sulfobetaine group, or a carboxybetaine group. For example, the zwitterionic group can have the structure

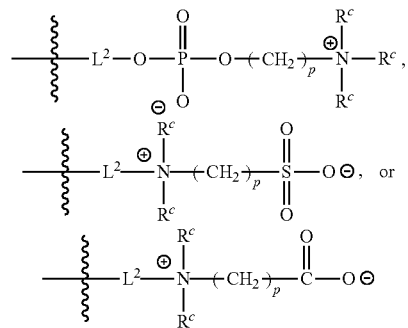

wherein $R^c$ is independently at each occurrence a substituted or unsubstituted $C_{1-12}$ alkyl group and p is independently at each occurrence an integer from 1 to 12 (e.g., p is 1, 2, 3, 4, 5, 6, 7, 8, 9, 10, 11, or 12). In some embodiments, each occurrence of $R^c$ is methyl. In some embodiments, p is an integer from 1 to 6, for example, in some embodiments p is equal to 2. In some embodiments, p is equal to 3.

In some embodiments, $R^3$ is preferably a phosphorylcholine zwitterionic group, for example a phosphorylcholine zwitterionic group of the formula

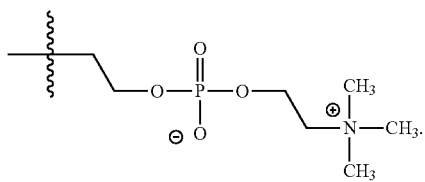

In some embodiments, $R^3$ is a poly($C_{1-6}$ alkylene oxide) group. For example, in some embodiments, $R^3$ can be a poly(ethylene oxide) group, a poly(propylene oxide) group, and the like, or a combination thereof. In some embodiments, $R^3$ can be a poly(ethylene oxide) group. For example, the poly(ethylene oxide) group can be of the formula

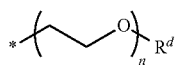

wherein n is an integer from greater than 1 to 50, for example 2 to 50, or 5 to 25, $R^d$ is a hydrogen or a $C_{1-6}$ alkyl group (e.g., a methyl group), and the "*" indicates the point of attachment of the ethylene oxide repeating unit to the polymer backbone (i.e., via V in formula (II)).

In some embodiments, $R^3$ can be a hydroxy-substituted $C_{1-6}$ alkyl group. In some embodiments, the $C_{1-6}$ alkyl group can be an ethylene group, and $R^3$ can be a 2-hydroxyethylene group. In some embodiments, the $C_{1-6}$ alkyl group can be a propylene group, and $R^3$ can be, for example, a 2-hydroxypropylene group.

In some embodiments, the repeating units comprising temozolomide are of formula (IV)

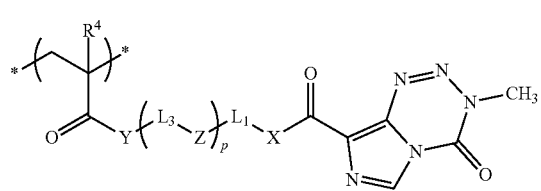

(IV)

wherein $R^4$ is independently at each occurrence a hydrogen or a $C_{1-6}$ alkyl group; Y is independently at each occurrence —O— or —NH—; $L^3$ is independently at each occurrence a divalent $C_{1-12}$ alkylene group, di($C_{1-12}$ alkylene) disulfide group (e.g., —($C_{1-12}$ alkylene)-S—S—($C_{1-12}$ alkylene)-), $C_{1-12}$ alkylene ester group (e.g., —($C_{1-12}$ alkylene)-(C=O)—O—), $C_{6-20}$ arylene group, or $C_{1-20}$ alkylene oxide group; Z is independently at each occurrence a disulfide group (e.g., —S—S—), a thioether group (e.g., —S—($C_{1-6}$ alkylene)-), a triazole group, a hydrazone group (e.g., —NH—N=CH—), or an amide group (e.g., —NH—(C=O)—); $L^1$ is independently at each occurrence a divalent $C_{1-12}$ alkylene group, di($C_{1-12}$) alkylene disulfide group, $C_{1-12}$ alkylene ester group, $C_{6-20}$ arylene group, $C_{1-20}$ alkylene oxide group, or $C_{1-12}$ alkylene sulfide group; X is independently at each occurrence —O— or —NH—; and p is independently at each occurrence 0 or 1.

In an embodiment, the polymer is a copolymer comprising repeating units of formula (II) and formula (IV) wherein in each occurrence of the repeating units of formula (II), $R^2$ is a methyl group; V is —O—; and $R^3$ is a phosphorylcholine group having the structure

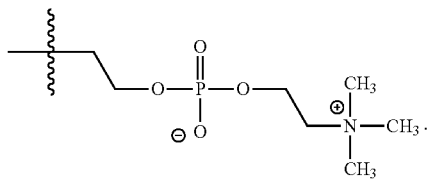

In each occurrence of the repeating units of formula (IV), $R^4$ is a methyl group; Y is —O—; p is 0; $L^1$ is a divalent $C_{1-6}$ alkylene group (e.g., an ethylene group); and X is —O—. For example, the copolymer can comprise repeating units of formula (IIA) and (IVA)

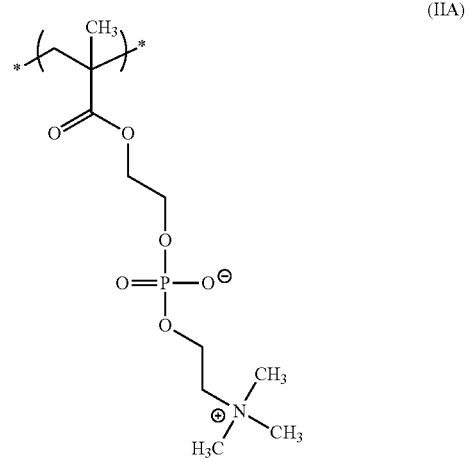

(IIA)

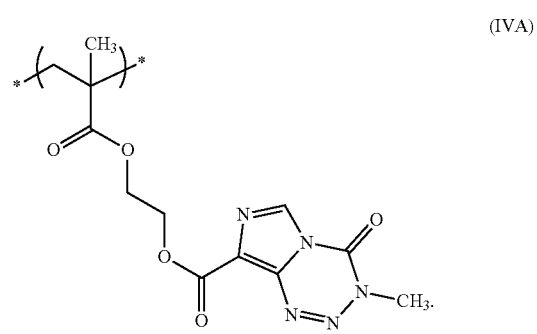

(IVA)

In an embodiment, the polymer is a copolymer comprising repeating units of formula (II) and formula (IV) wherein in each occurrence of the repeating units of formula (II), $R^2$ is a methyl group; V is —O—; and $R^3$ is a phosphorylcholine group having the structure

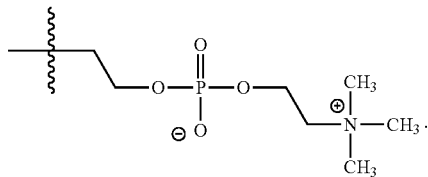

In each occurrence of the repeating units of formula (IV), $R^4$ is a methyl group; Y is —O—; p is 0; $L^1$ is a divalent di($C_{1-6}$ alkylene) disulfide group (e.g., a —($C_2H_4$)—S—S—($C_2H_4$)— group); and X is —O—. For example, the copolymer can comprise repeating units of formula (IIA) and (IVB)

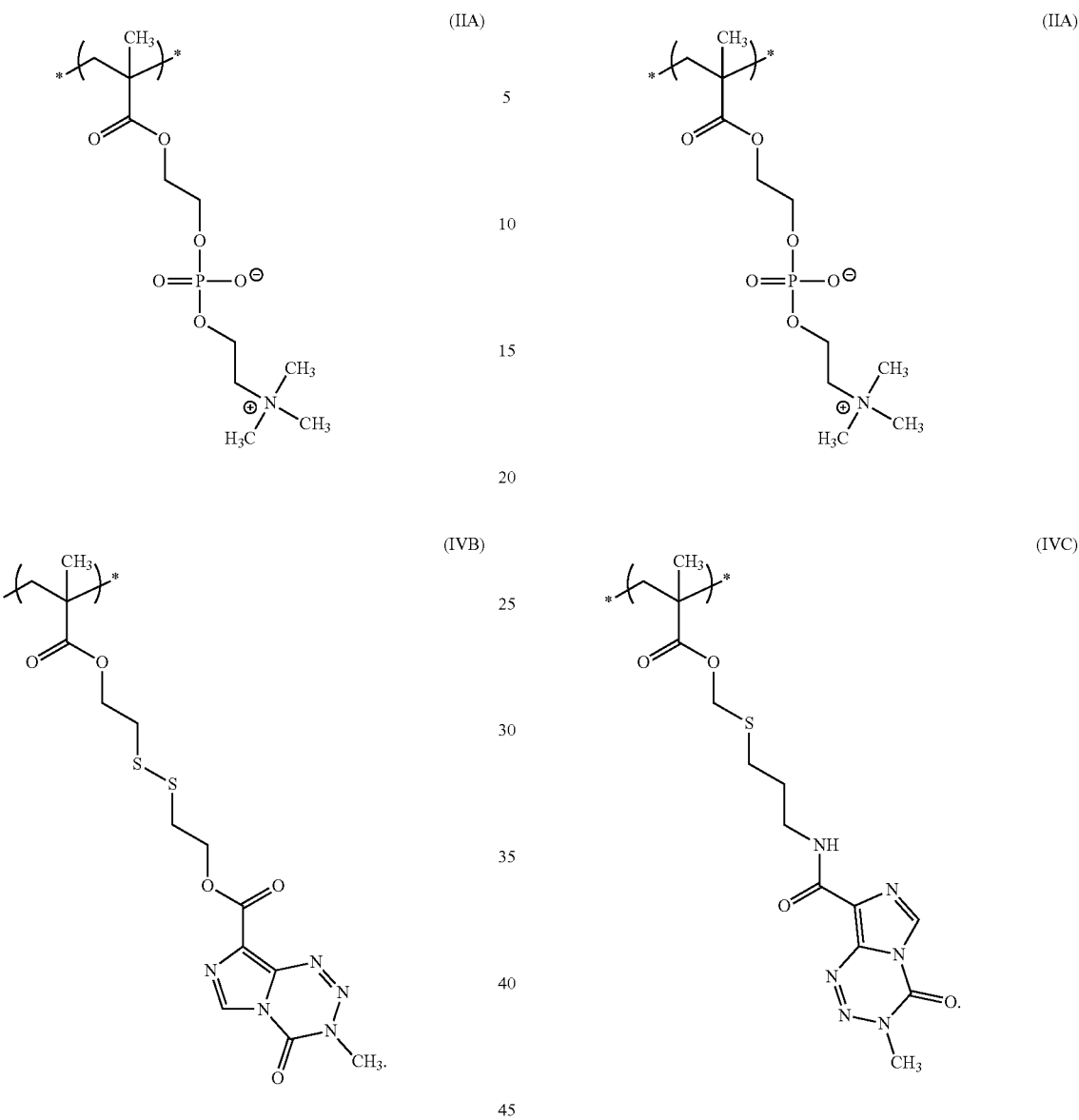

In an embodiment, the polymer is a copolymer comprising repeating units of formula (II) and formula (IV) wherein in each occurrence of the repeating units of formula (II), $R^2$ is a methyl group; V is —O—; and $R^3$ is a phosphorylcholine group having the structure

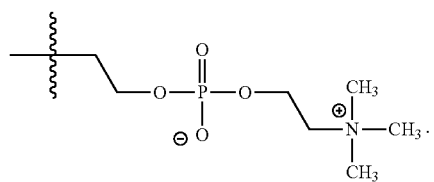

In each occurrence of the repeating units of formula (IV), $R^4$ is a methyl group; Y is —O—; p is 1; $L^3$ is a divalent $C_{1-6}$ alkylene group; Z is a $C_{1-6}$ thioether group (e.g., —S—($C_{1-6}$ alkylene)-); $L^1$ is a divalent $C_{1-6}$ alkylene group (e.g., a propylene group); and X is —NH—. For example, the copolymer can comprise repeating units of formula (IIA) and (IVC)

In an embodiment, the polymer is a copolymer comprising repeating units of formula (II) and formula (IV) wherein in each occurrence of the repeating units of formula (II), $R^2$ is a methyl group; V is —O—; and $R^3$ is a phosphorylcholine group having the structure

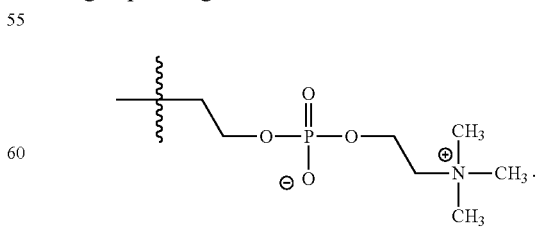

In each occurrence of the repeating units of formula (IV), $R^4$ is a methyl group; Y is —O—; p is 1; $L^3$ is a divalent $C_{1-20}$ alkylene oxide group; Z is a triazole group of the formula

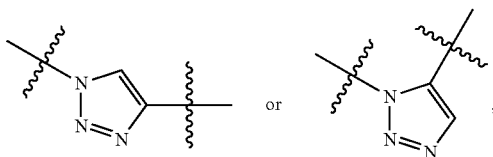

$L^1$ is a divalent $C_{1-6}$ alkylene group (e.g., a methylene group); and X is —NH—. For example, the copolymer can comprise repeating units of formula (IIA) and (IVD)

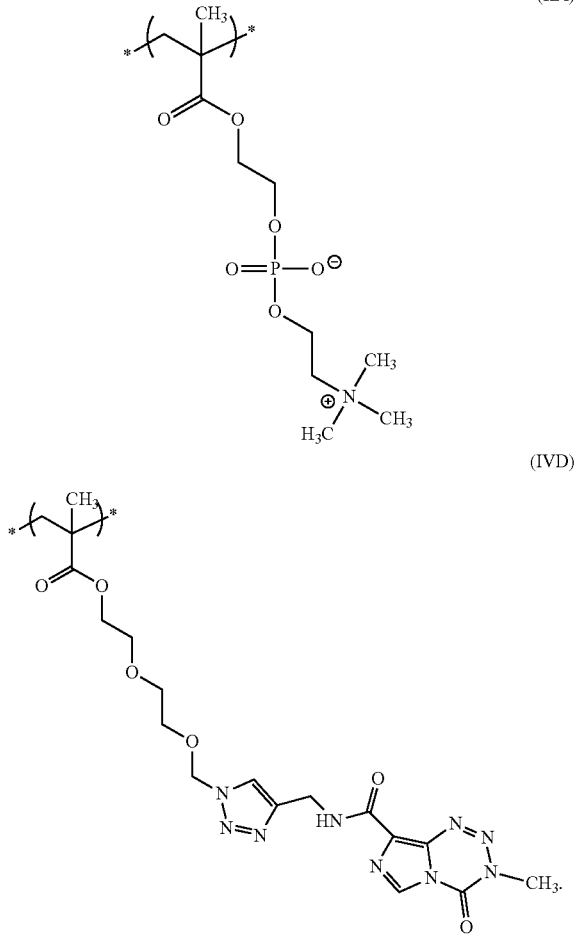

In an embodiment, the polymer is a copolymer comprising repeating units of formula (II) and formula (IV) wherein in each occurrence of the repeating units of formula (II), $R^2$ is a methyl group; V is —O—; and $R^3$ is a phosphorylcholine group having the structure

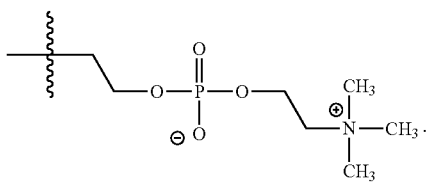

In each occurrence of the repeating units of formula (IV), $R^4$ is a methyl group; Y is —O—; p is 1; $L^3$ is a divalent $C_{1-6}$ alkylene group (e.g., a methylene group); Z is a hydrazone group (e.g., —(C=O)—NH—N=CH—); $L^1$ is a divalent $C_{1-6}$ alkylene group (e.g., an ethylene group); and X is —O—. For example, the copolymer can comprise repeating units of formula (IIA) and (IVE)

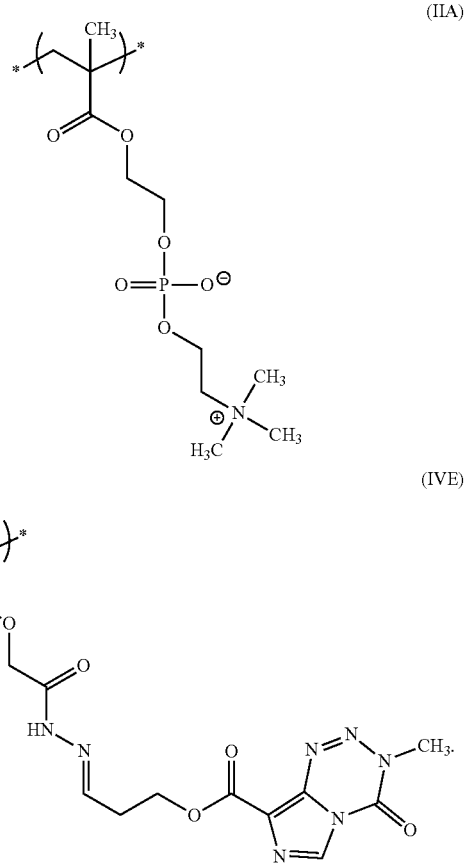

In an embodiment, the polymer is a copolymer comprising repeating units of formula (II) and formula (IV) wherein in each occurrence of the repeating units of formula (II), $R^2$ is a methyl group; V is —O—; and $R^3$ is a phosphorylcholine group having the structure

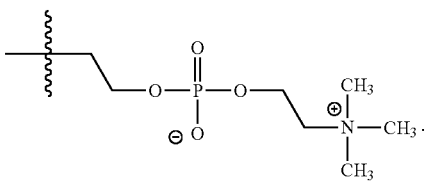

In each occurrence of the repeating units of formula (IV), $R^4$ is a methyl group; Y is —O—; p is 0; and X is —NH—.

In an embodiment, the polymer is a copolymer comprising repeating units of formula (II) and formula (IV) wherein in each occurrence of the repeating units of formula (II), $R^2$ is a methyl group; V is —O—; and $R^3$ is a phosphorylcholine group having the structure

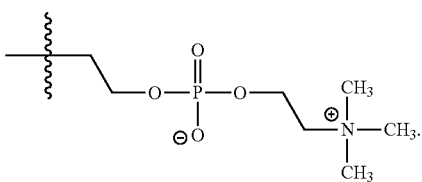

In each occurrence of the repeating units of formula (IV), $R^4$ is a methyl group; Y is —O—; p is 1; $L^3$ is a divalent $C_{1-12}$ alkylene group; Z is a disulfide group; $L^1$ is a divalent $C_{1-6}$ alkylene group; and X is —NH—.

In some embodiments, the copolymer can include 1 to 60 mole percent, or 5 to 55 mole percent, or 10 to 55 mole percent, or 15 to 55 mole percent of repeating units comprising temozolomide (e.g., repeating units according to formula (IV)), based on the total moles of repeating units of the copolymer. The total amount of repeating units comprising temozolomide can be determined using known techniques, for example, using proton nuclear magnetic resonance ($^1$H NMR) spectroscopy or UV/Vis spectroscopy.

In some embodiments, the copolymer can have a number average molecular weight of 1,000 to 100,000 grams per mole, or 5,000 to 100,000 grams per mole, or 5,000 to 50,000 grams per mole, or 10,000 to 50,000 grams per mole, or 10,000 to 40,000 grams per mole, or 10,000 to 30,000 grams per mole, or 20,000 to 30,000 grams per mole. In some embodiments, the copolymer can have a polydispersity index (PDI) of less than or equal to 2, for example 1 to 2, or 1 to 1.75, or 1 to 1.5 or 1 to 1.2, or 1 to 1.1. Molecular weight and PDI can be determined, for example, using gel permeation chromatography (GPC), as described further in the working examples below.

In some embodiments, the copolymer can be a random copolymer. In some embodiments, the copolymer can be a block copolymer. In some embodiments, the copolymer is a diblock copolymer comprising repeating units according to formula (II) and (IV). In some embodiments, the copolymer comprises less than or equal to 10 mole percent, or less than 5 mole percent, or less than 1 mole percent of repeating units other than the repeating units according to formulas (II) and (IV).

In some embodiments, the copolymer is water soluble. For example, in some embodiments, the copolymer has a water solubility of at least 10 milligrams per milliliter, or at least 25 milligrams per milliliter, or at least 50 milligrams per milliliter, or at least 100 milligrams per milliliter.

In some embodiments, the copolymer can be crosslinked. Crosslinking of the copolymer can be achieved, for example, by copolymerization with a difunctional monomer (e.g., a dimethacrylate monomer) or the like, or by a post-polymerization reaction using an appropriate crosslinker. Crosslinking of the copolymers can, in some embodiments, provide a crosslinked polymer gel, that is swellable, but not soluble, in an aqueous solution. In some embodiments, crosslinking of the copolymer can be carried out such that crosslinked polymer nanoparticles comprising the copolymer are the result. Such polymer nanoparticles can have, for example, an average diameter of less than or equal to 100 nanometers, or 1 to 100 nanometers, or 10 to 100 nanometers, or 10 to 50 nanometers. Preferably, the polymer nanoparticles comprising the copolymer are dispersible in water.

The copolymers of the present disclosure can be prepared using methods which are generally known. For example, the copolymers can be prepared using free radical polymerization techniques, for example controlled free radical polymerization techniques (e.g., reversible addition-fragmentation chain-transfer polymerization (RAFT), and the like). An example of the method of making the copolymer is further described in the working examples below.

The structure of the repeating units comprising temozolomide will be dictated by the particular temozolomide derivative selected for preparation of the copolymer. For example, the chemistry used to provide the repeating units comprising temozolomide (and thus the resulting repeating unit structure) can be selected depending on the particular $R^1$ group present on the temozolomide compound and, if necessary, the complementary reactive group present on the copolymer (e.g., if post-polymerization functionalization is used).

For example, in some embodiments, when a polymerizable group such as an acrylate, methacrylate, acrylamide, or methacrylamide is present on the temozolomide compound, the copolymer can be prepared directly by copolymerization of the temozolomide compound with the desired comonomer to provide the copolymer comprising repeating units of formula (II) and (IV).

In some embodiments, a copolymer precursor can be prepared, wherein the precursor comprises repeating units of formula (II) and further comprises repeating units comprising a functional group that is reactive towards the $R^1$ group of the temozolomide compound to be conjugated to the precursor to provide the desired copolymer (i.e., the copolymer comprising repeating units of formula (II) and (IV)). For example, a copolymer precursor can comprise repeating units of formula (II) and repeating units comprising an alkenyl group (e.g., when $R^1$ of the temozolomide compound is a thiol, and the temozolomide compound can be conjugated to the precursor using a thiol-ene reaction), a thiol group (e.g., when the $R^1$ of the temozolomide compound is an alkenyl group or a thiol group, and the temozolomide compound can be conjugated to the precursor using a thiol-ene reaction or via disulfide formation, respectively), an azide group (e.g., when $R^1$ of the temozolomide compound is an alkynyl group, and the temozolomide compound can be conjugated to the precursor using copper mediated azide-alkyne click chemistry), or a hydrazide group (e.g., when $R^1$ of the temozolomide compound is an aldehyde or ketone, and the temozolomide compound can be conjugated to the precursor via hydrazone formation).

The functionalized temozolomide compounds can also be conjugated to polymers not based on a (meth)acrylate polymer backbone. For example, the functional temozolomide compounds can also be conjugated to a polymer chain end, for example a poly(ethylene glycol) chain end). Thus, another aspect of the present disclosure is a poly(ethylene glycol)-temozolomide conjugate comprising a poly(ethylene glycol) having at least two chain ends conjugated to a temozolomide compound.

The poly(ethylene glycol) can be a linear poly(ethylene glycol) (i.e., having two chain ends) or a multi-arm branched or star poly(ethylene glycol) (i.e., having more than 2 chain ends). In some embodiments, the poly(ethylene glycol) having at least two chain ends conjugated to a temozolomide compound is of formula (V) or (VI)

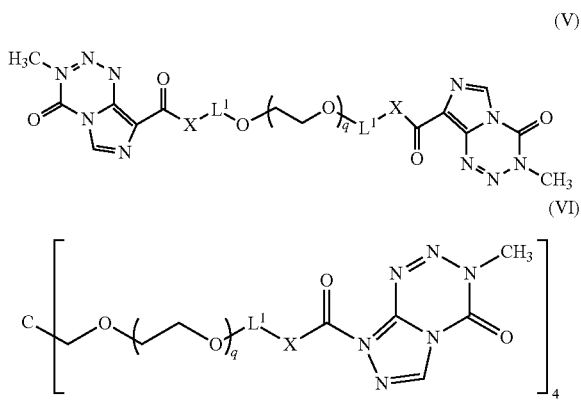

wherein X is independently at each occurrence —O— or —NH—; $L^1$ is independently at each occurrence a divalent $C_{1-12}$ alkylene group, di($C_{1-12}$ alkylene) disulfide group, $C_{1-12}$ alkylene ester group, $C_{6-20}$ arylene group, $C_{1-20}$ alkylene oxide group, or $C_{1-12}$ alkylene sulfide group; and q is an integer from 1 to 500, or 1 to 250, or 1 to 100, or 1 to 50, or 1 to 25. In some embodiments, X is —O— and $L^1$ is a divalent di($C_{1-12}$ alkylene) disulfide group. In some embodiments, X is —NH— and $L^1$ is a divalent $C_{1-12}$ alkylene sulfide group.

As described above, the polymers described herein comprising temozolomide are thought to be particularly useful in the treatment of certain cancers. Thus, another aspect of the present disclosure is a method of treating a disease. The method comprises administering a therapeutically effective amount of a composition comprising the above described polymer. The composition can include 1 to 100 weight percent of the polymer, based on the total weight of the composition. The composition can be, for example, an aqueous composition comprising the copolymer and an aqueous solution (e.g., water, a physiological saline solution, a sugar solution, or combinations thereof). The composition can be administered to a subject having the disease to be treated. The subject can be a mammal, for example, a human, a mouse, or a rat. In some embodiments, the disease to be treated is cancer, in particular, metastatic melanoma, high grade glioma, glioblastoma and other brain cancers, lung cancer, breast cancer, testicular cancer, colon and rectal cancers, carcinomas, sarcomas, lymphomas, leukemias, and mycosis fungoides. In some embodiments, the disease is brain cancer, in particular, high grade glioma, glioblastoma, and the like. Administration of the composition comprising the polymer can be, for example, by injection, in particular intravenous injection, subcutaneous injection, or intraperitoneal injection, oral administration, or by implantation (e.g., of an implant device comprising the composition comprising the TMZ-containing polymer, preferably wherein the TMZ-containing polymer is not water-soluble). In some embodiments, administering the composition is preferably by intravenous injection. The therapeutically effective amount can be, for example, 75 to 200 milligrams of TMZ per square meter of body surface area of the subject. Administration of the composition can be determined based on the needs of the subject, and can be of varying frequency, for example once per day, multiple (2 or more) times per day, once every three days, or any other desired dosing frequency. The composition comprising the polymer can optionally further comprise one or more anti-cancer (e.g., anti-brain cancer) ingredients or other additives to further enhance the efficacy of the composition or assist in manufacturing or storage of the composition, with the proviso that any additional anti-cancer ingredient or additive is selected so as to not have significant adverse effects on the efficacy of the polymer comprising temozolomide.

The temozolomide compounds, polymers, and methods described herein are further illustrated by the following non-limiting examples.

EXAMPLES

The examples described herein utilize a novel methacrylate derivative of TMZ, whereby TMZ was incorporated as pendent moieties in copolymers of poly(2-methacryloyloxyethyl phosphorylcholine) (polyMPC), a water-soluble biomaterial that has shown excellent utility for sustained chemotherapy. See, e.g., Wong, K. E.; Mora, M. C.; Skinner, M.; McRae Page, S.; Crisi, G. M.; Arenas, R. B.; Schneider, S. S.; Emrick, T. Evaluation of PolyMPC-Dox Prodrugs in a Human Ovarian Tumor. Mol. Pharmaceutics 2016, 13, 1679-1687; McRae Page, S.; Henchey, E.; Chen, X.; Schneider, S.; Emrick, T. Efficacy of PolyMPC-DOX Prodrugs in 4T1 Tumor-Bearing Mice. Mol. Pharmaceutics 2014, 11, 1715-1720. Copolymerization, achieved using reversible addition-fragmentation chain-transfer (RAFT) chemistry, afforded polyMPC-TMZ conjugates with tunable drug incorporations and narrow, well-defined molecular weight distributions.

FIG. 1 depicts the synthesis of TMZ methacrylate (shown as compound 2). Room temperature diazotization and subsequent hydrolysis of the exocyclic carbamoyl was accomplished using nitrous acid, generated in situ at 0° C. from water, concentrated sulfuric acid, and sodium nitrite. Precipitation over ice afforded TMZ-carboxylic acid (shown as compound 1) as a fine white solid in yields of up to 79%. Disappearance of resonances corresponding to primary amide protons in the proton nuclear magnetic resonance ($^1$H-NMR) spectrum indicated complete carbamoyl hydrolysis, and electron ionization high-resolution mass spectrometry (HRMS-EI) confirmed the expected structure of compound 1 ([M]$^+$: 195.0395 g/mol).

Figure 2:
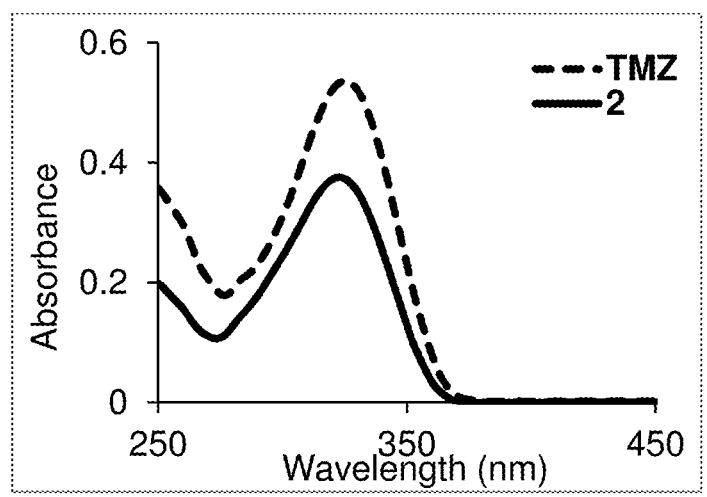
FIG. 2 shows the UV/Vis absorption spectra of TMZ and compound 2 in trifluoroethanol at concentrations of 0.01 milligrams per milliliter (mg/ml).
Figure 3:
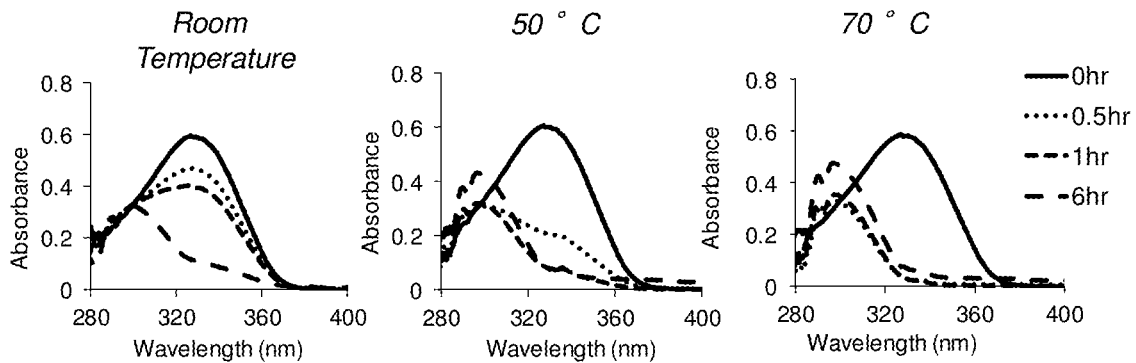
FIG. 3 shows the UV-Vis absorption spectra of TMZ in 1:1 methanol:dimethylsulfoxide (MeOH:DMSO) at 0.01 mg/ml. Solutions were stirred at room temperature, 50° C., or 70° C. and analyzed at designated times.

Esterification chemistry was used, as shown in FIG. 1, to provide TMZ-methacrylate (shown as compound 2) by the reaction of compound 1 and 2-hydroxyethyl methacrylate (HEMA) in the presence of 1-(3-dimethylaminopropyl)-3-ethylcarbodiimide hydrochloride (EDC) and catalytic 4-dimethylaminopyridine (DMAP). Given the poor solubility of compound 1 in organic solvents, esterification was performed in dichloromethane (DCM) suspensions. Impurities and excess reagents were readily removed by silica gel chromatography, yielding pure compound 2, as confirmed by fast-atom bombardment HRMS (HRMS-FAB) ([M+H]$^+$: 308.0989 g/mol), in 54% yield. Spectroscopy further demonstrated integrity of the imidazotetrazine heterocycle. In the $^1$H-NMR spectrum of compound 2, resonances corresponding to imidazole (peak e, δ=8.85 ppm) and methyltriazene (peak f, δ=3.88 ppm) protons were observed, and UV-Vis absorption spectra of TMZ ($λ_{max}$=325 nm) and derivative 2 ($λ_{max}$=323 nm) were found to be equivalent (as shown in FIG. 2).

Copolymerization of MPC and TMZ-methacrylate by RAFT was initially attempted in a mixture of methanol (MeOH) and dimethylsulfoxide (DMSO), a mixture that proved useful for homogeneity of the reaction mixture. Although monomer conversion was high (87%), as estimated by $^1$H-NMR spectroscopy, characterization of the isolated copolymer by UV-Vis spectroscopy showed a significant shift in absorption maximum ($\lambda_{max}$=287 nm), a spectral change indicative of TMZ decomposition. This observation prompted investigation of the stability of TMZ in organic solvents, a property not previously reported to our knowledge. Solutions of TMZ (0.01 milligram per milliliter concentration) in 1:1 MeOH:DMSO, DMSO, ACN, and 2,2,2-trifluoroethanol (TFE) were incubated at room temperature, as well as elevated temperatures (e.g., 50° C. and 70° C.). Analysis by UV-Vis spectroscopy, shown in FIGS. 3-6, showed that the absorption spectrum of TMZ remained unchanged after 24 hour incubation in DMSO and ACN at all temperatures. In contrast, TMZ heated at 50° C. or 70° C. in the MeOH:DMSO mixture fully degraded after only 1 hour, with significant degradation observed even at room temperature. Importantly, TMZ was found to be stable in TFE, also a good solvent for polyzwitterions, at temperatures up to 70° C. for greater than 24 hours. The marked difference in stability of TMZ observed between MeOH and TFE was attributed to the poor nucleophilicity of the latter, which precludes rapid imidazotetrazine solvolysis.

Figure 7:
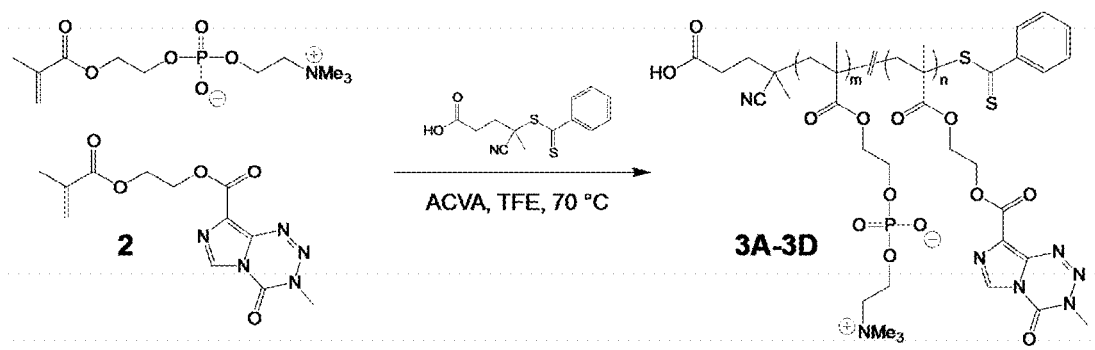
FIG. 7 is a chemical scheme depicting the copolymerization of methacryloyloxyethyl phosphorylcholine (MPC) and TMZ-methacrylate.

Based on the solvent studies, TFE was selected as the solvent for RAFT polymerization in the following examples. A schematic illustration of the RAFT polymerization of MPC and TMZ-methacrylate is shown in FIG. 7.

Figure 4:
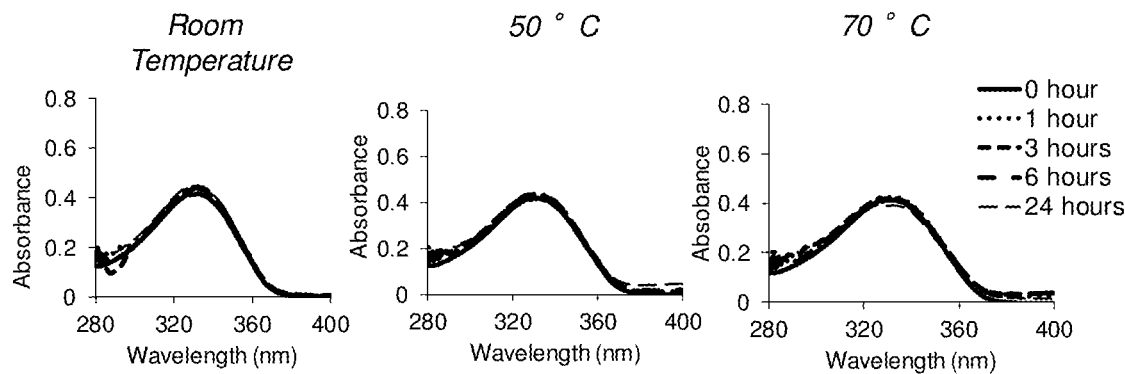
FIG. 4 shows the UV-Vis absorption spectra of TMZ in DMSO at 0.01 mg/ml. Solutions were stirred at room temperature, 50° C., or 70° C. and analyzed at designated times.
Figure 5:
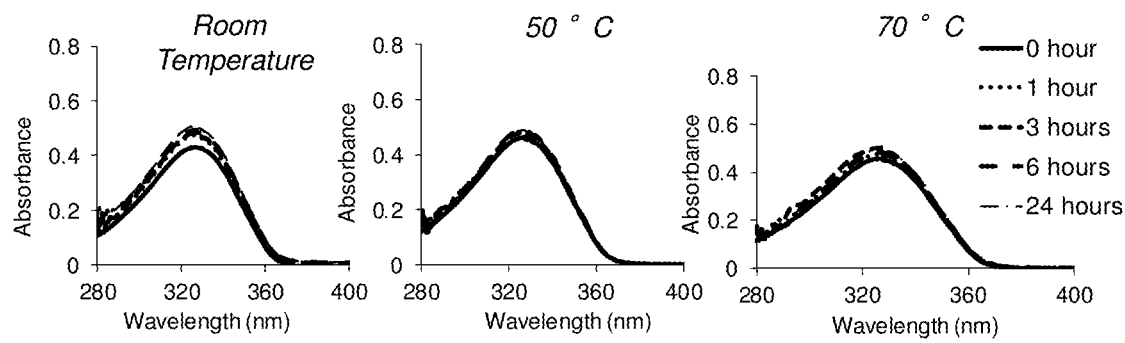
FIG. 5 shows the UV-Vis absorption spectra of TMZ in acetonitrile (ACN) at 0.01 mg/ml. Solutions were stirred at room temperature, 50° C., or 70° C. and analyzed at designated times.
Figure 6:
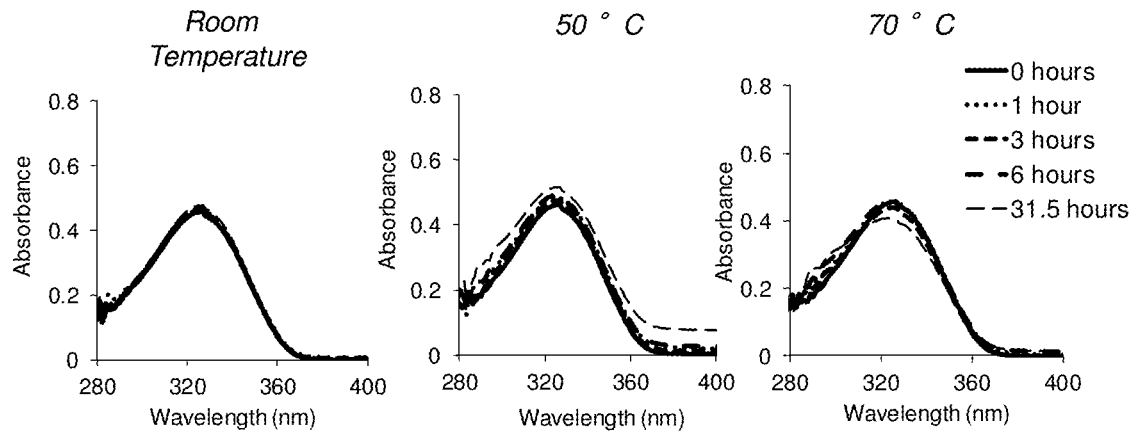
FIG. 6 shows the UV-Vis absorption spectra of TMZ in trifluoroethanol (TFE) at 0.01 mg/ml. Solutions were stirred at room temperature, 50° C., or 70° C. and analyzed at designated times.

Copolymerizations of MPC and compound 2 were performed at 70° C. in TFE, as shown in FIG. 4, utilizing 4,4'-azobis(4-cyanovaleric acid) (ACVA) and 4-cyano-4-(phenylcarbonothioylthio)pentanoic acid as radical initiator (I) and chain-transfer agent (CTA), respectively. Reagent stoichiometry was established to yield copolymers with approximate number-average molecular weights ($M_n$) of 20,000 grams per mole (g/mole), and monomer feed ratios were intended to target incorporations of compound 2 of 11 (Polymer 3A), 21 (Polymer 3B), 35 (Polymer 3C), and 50 (Polymer 3D) mole percent. Monomer conversions of 88-94% were achieved with polymerization times of 6 to 9 hours. After quenching polymerizations by exposure to air, the crude polymer products were purified by repeated precipitation from TFE into excess THF, followed by centrifugal dialysis against aqueous 0.1 molar (M) hydrochloric acid. Purified conjugates were lyophilized, giving Polymers 3A-3D as pink solids in yields of 60-74%.

Figure 8:
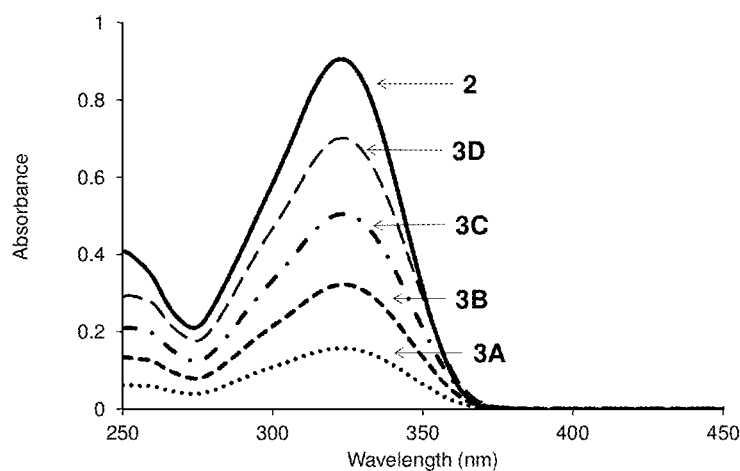
FIG. 8 shows the UV-Vis absorption spectra of polyMPC-TMZ copolymers in TFE.
Figure 9:
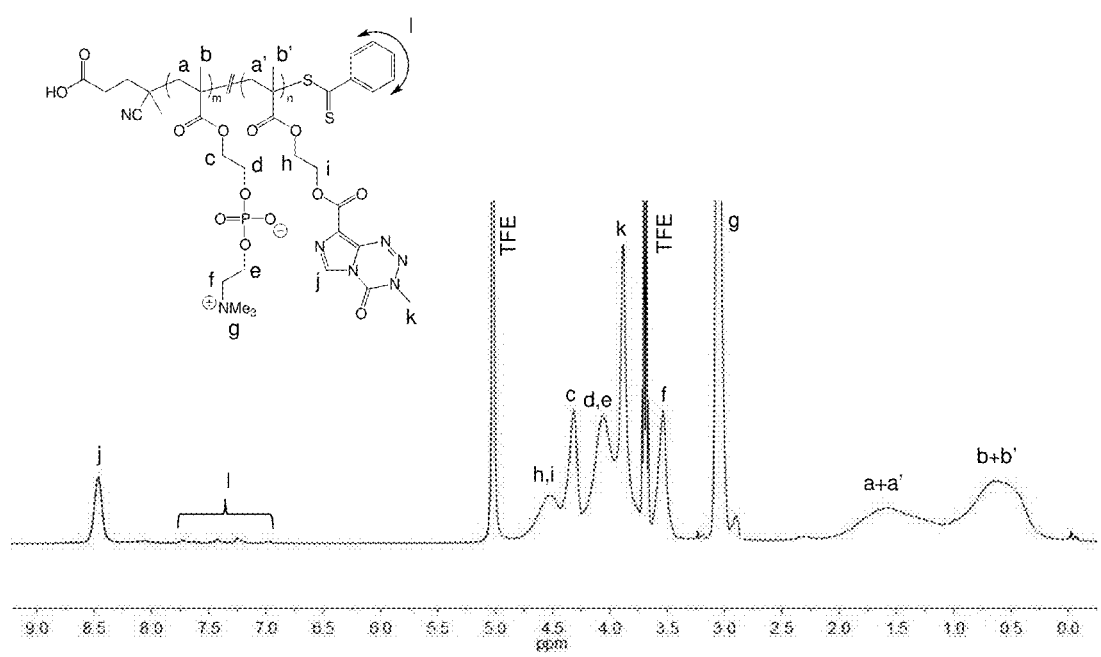
FIG. 9 shows the $^1$H-NMR (500 MHz) spectrum of polyMPC-TMZ (3D) obtained in deuterated trifluoroethanol (TFE-d$_3$).

UV-Vis and NMR spectroscopy were performed to demonstrate successful incorporation of pendent TMZ in copolymers 3A-3D. FIG. 8 shows UV-Vis absorption spectra of conjugates 3A-3D. Each copolymer shows an absorption maximum at 323 nanometers (nm), with no spectral features indicative of TMZ degradation. In the $^1$H-NMR spectrum of copolymer 3D, shown in FIG. 9, resonances corresponding to intact imidazole (region "j", δ=8.34-8.64 ppm) and methyltriazene (peak "k", δ=3.89 ppm) groups are clearly observed. Additionally, carbon resonances at 140.88, 131.41, and 38.03 parts per million (ppm) are present in the $^{13}$C-NMR spectrum of 3D that correspond to urea, imidazole, and methyltriazene moieties, respectively, confirming TMZ fidelity. Each copolymer possesses an absorption maximum at 323 nm, with a notable absence of any spectral features that would otherwise suggest TMZ degradation.

Using $^1$H-NMR spectroscopy, copolymer compositions were estimated by comparing relative signal intensities of the imidazole and trimethylammonium (region "g", δ=2.80-3.30 ppm) groups. Additionally, incorporation of compound 2 was estimated by measuring UV-Vis absorption at λ=323 nm for solutions of 3A-3D in TFE. The weight percent of compound 2 in the polyMPC-TMZ copolymers was then determined using a calibration curve. Estimated incorporations of compound 2 are summarized in Table 1. In general, the copolymer compositions estimated using both spectroscopic techniques were in reasonable agreement with the theoretical values.

TABLE 1

| Polymer | Target incorporation of compound 2 (mol %) | Target incorporation of compound 2 (wt %) | Measured incorporation of compound 2 by NMR (mol %)[a] | Measured incorporation of compound 2 by UV/Vis (wt %)[b] |
|---|---|---|---|---|
| 3A | 11 | 11 | 16 | 8 |
| 3B | 21 | 21 | 25 | 17 |
| 3C | 35 | 36 | 37 | 27 |
| 3D | 50 | 52 | 52 | 38 |

[a]Molar incorporations estimated by $^1$H-NMR (500 MHz) spectroscopy in TFE-$d_3$.
[b]Mass incorporation estimated by UV-Vis spectroscopy of TFE solutions at polymer concentrations of 0.05 mg/ml.

Figure 10:
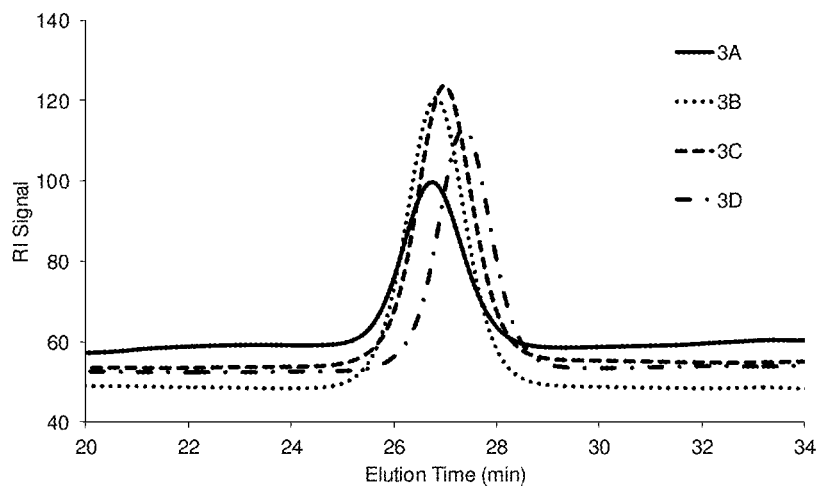
FIG. 10 shows the gel permeation chromatograms of polymers 3A-3D, obtained by gel permeation chromatography (GPC) eluting with TFE.
Figure 11:
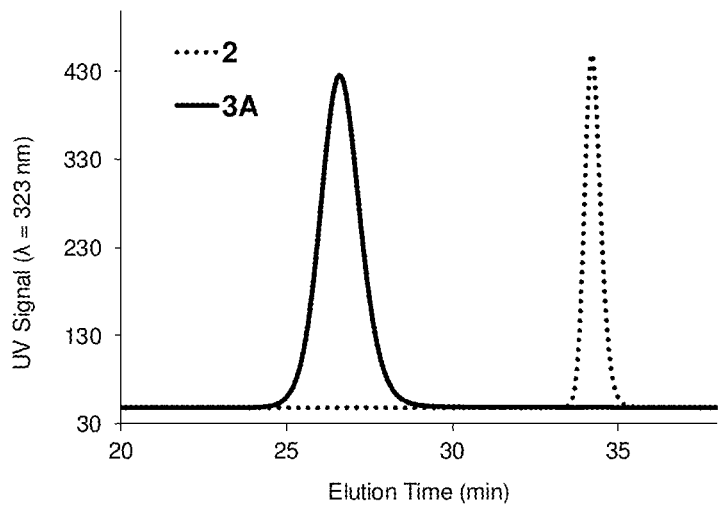
FIG. 11 shows TFE GPC chromatograms of compound 2 and polymer 3A with detection by UV-Vis absorbance at λ=323 nm. For copolymer 3A, a single polymer fraction was observed (elution time of 26.6 minutes), with a notable absence of residual compound 2 (elution time of 34.2 minutes). The chromatogram of 3A is representative of copolymers 3B-3D.

Molecular weight characterization of Polymers 3A-3D was performed by gel permeation chromatography (GPC) eluting in TFE, and molecular weight distributions were observed to be narrow and monomodal, as shown in FIG. 10. Copolymers were prepared with low PDI values, estimated relative to poly(methyl methacrylate) calibration standards, and estimated $M_n$ values were in reasonable agreement with those targeted. Additionally, GPC chromatograms of polyMPC-TMZ copolymers obtained using detection by UV absorbance showed a notable absence of residual (i.e., unconjugated) compound 2, confirming conjugate purity, as shown in FIG. 11. This molecular weight characterization demonstrates that the RAFT polymerization strategy is amenable to preparing well-defined polymer-TMZ conjugates using compound 2 as a comonomer.

TABLE 2

| Polymer | Mn (theoretical) (g/mol) | Mn (GPC) (g/mol) | PDI |
|---|---|---|---|
| 3A | 20,160 | 28,730 | 1.09 |
| 3B | 19,050 | 27,920 | 1.10 |
| 3C | 19,410 | 25,860 | 1.09 |
| 3D | 19,880 | 21,880 | 1.08 |

Figure 12:
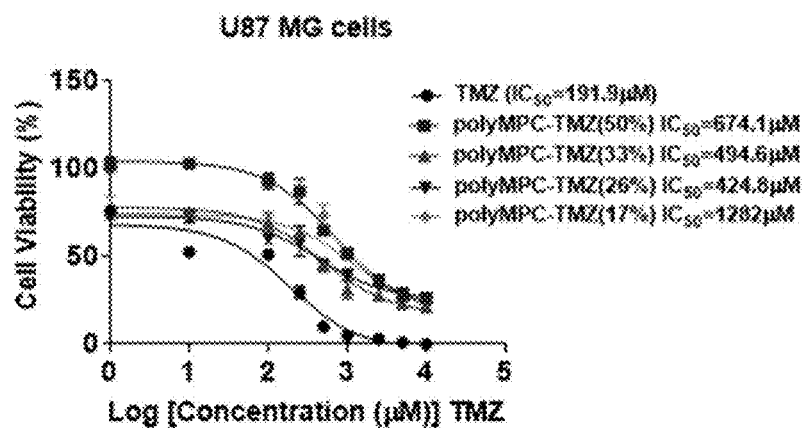
FIG. 12 shows cell viability of U87MG cells in the presence of different PolyMPC-TMZ conjugates (random co-polymers).
Figure 13:
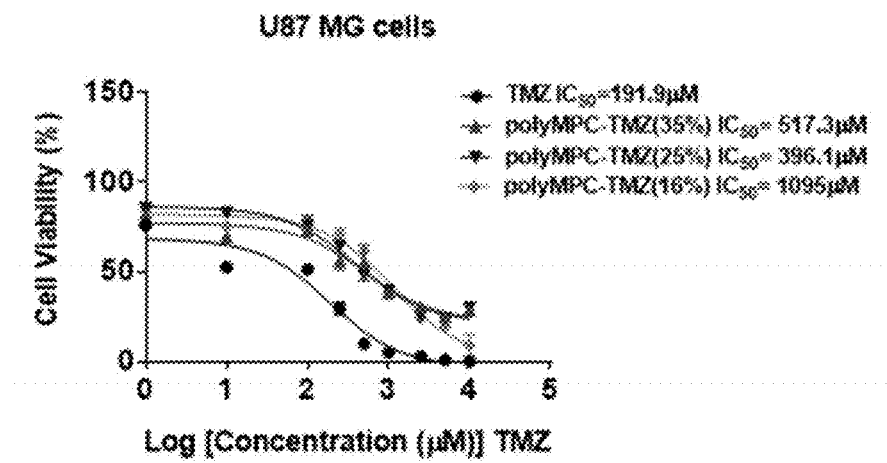
FIG. 13 shows cell viability of U87MG cells in the presence of different PolyMPC-TMZ conjugates (block co-polymers).

Testing of the cytotoxic effects of polyMPC-TMZ on glioblastoma (GBM) cell lines utilized U87MG (TMZ sensitive cell line) and T98G (TMZ-resistant cell line). PolyMPC-TMZ random and block copolymers were tested with each cell line, as shown in FIGS. 12 and 13, respectively. U87MG cells were plated on 96 well plates and cultured overnight in DMEM media containing 10% FBS at 37° C. in a $CO_2$ incubator. The cells were treated with different doses of TMZ (0-10000 μM), polyMPC-TMZ-17% (random copolymer with 17 mole percent TMZ monomer) (0-10000 μM), polyMPC-TMZ-26% (random copolymer with 26% TMZ monomer) (0-10000 μM), polyMPC-TMZ-33% (random copolymer with 33% TMZ monomer) (0-10000 μM) or polyMPC-TMZ-50% random copolymer with 50 mole percent TMZ monomer) (0-10000 μM) and cell viability was tested on Day 7 using the CellTiter-Glo luminescent cell viability assay purchased from Promega, Inc. PolyMPC itself was used as a control polymer. Dose response curves were generated and the $IC_{50}$ value for TMZ was ~192 μM while polyMPC itself exhibited no toxicity whatsoever. All of the polyMPC-TMZ conjugates were efficacious, with a modified toxicity response as is typical of polymer prodrugs which mask the toxicity of the drug prior to making them available to the tumor. PolyMPC-TMZ conjugates containing 26-50 mole percent TMZ had $IC_{50}$ values of approximately 2-3 times that of TMZ itself (1282 µM, 424.8 µM, 494.6 µM, and 674.1 µM for polyMPC-TMZ containing 17, 26, 33, and 50% TMZ, respectively, for random copolymers, and 1095 µM, 396.1 µM, and 517.3 µM for polyMPC-TMZ containing 16, 25, and 35% TMZ, respectively, for block copolymers). The higher $IC_{50}$ values of polyMPC-TMZ will allow for introduction of larger drug doses in in vivo experiments.

Figure 14:
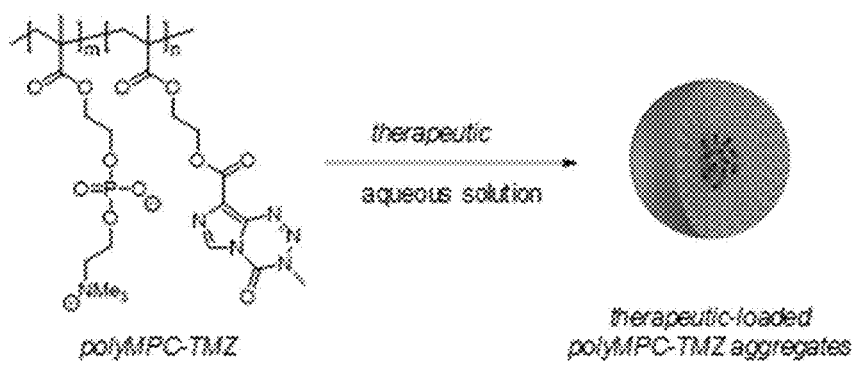
FIG. 14 is a schematic illustration showing the encapsulation of a therapeutic in a polyMPC-TMZ nanoparticle.

The polyMPC-TMZ conjugates were found to aggregate into polymeric nanoparticles in aqueous solution due to sequestration of the hydrophobic TMZ, forming a core-type structure, surrounded by water-soluble polyMPC corona, as illustrated schematically in FIG. 14. Such aggregates are useful for further encapsulation of additional therapeutic agents, for example additional, non-conjugated TMZ, $O^6$-benzylguanine, or doxorubicin. In this process, the drugs are solubilized by mixing them with aqueous polyMPC-TMZ suspensions, leading to solubilization of the drugs by loading into the TMZ-rich core of polyMPC-TMZ structures. The TMZ example serves as a facile method for amplifying TMZ loading, while the use of $O^6$-benzylguanine is intended to sensitize TMZ-resistant glioblastoma cells. Doxorubicin, a chemotherapeutic which has shown activity against glioblastoma in cell culture, can be loaded into the aggregates using the cytotoxic polyMPC-TMZ amphiphiles for a dual therapeutic.

Figure 15:
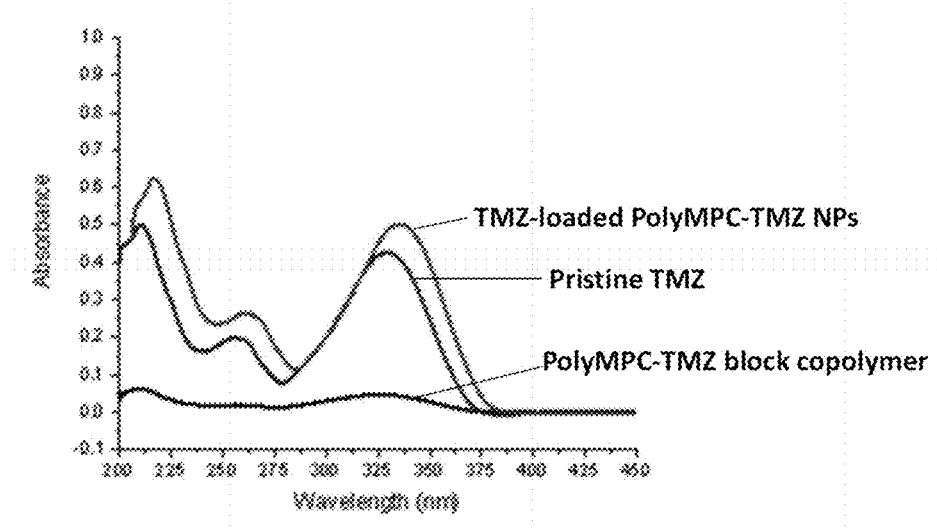
FIG. 15 shows UV-Vis spectra of a polyMPC-TMZ block copolymer, pristine TM), and TMZ-loaded polyMPC-TMZ NPs. The increase in absorbance for the TMZ-characteristic absorption (λ=328-336 nm) confirms TMZ encapsulation in the nanoparticles.

In an exemplary preparation of TMZ-loaded polyMPC-TMZ nanoparticles, an aqueous solution of a polyMPC-TMZ block copolymer with a concentration of 5 mg/mL was added to a vial containing TMZ powder (3.5 mg). The suspension was subjected to vortexing for 1-2 minutes to afford a homogenous suspension with no evidence of residual TMZ powder. The suspension was filtered through a 0.45 micron cellulose acetate filtere, and the TMZ-loaded NPs were analyzed by UV-Vis spectroscopy. A significant increase in the absorbance of the characteristic TMZ peak ($\lambda$=328-336 nm), along with a red-shift in the absorption maximum ($\lambda_{polyMPC-TMZ}$=328 nm→$\lambda_{NPs}$=336 nm), suggests TMZ encapsulation into the polyMPC-TMZ core, as shown in FIG. 15.

Thus, TMZ, a first-line chemotherapeutic indicated for treating glioblastoma, was successfully incorporated into a series of polyMPC conjugates by controlled RAFT copolymerization utilizing a novel TMZ-methacrylate derivative. TMZ was introduced as a pendent moiety in a tunable fashion at drug loadings of greater than 50 mole percent, and conjugates were prepared with narrow and controlled molecular weight distributions. This synthetic demonstration reveals a method for preparing well-defined TMZ-containing polymer therapeutics using simple and effective polymerizations that are metal-free. Moreover, owing to the ubiquitous reactivity of the TMZ-methacrylate derivative, opportunities for introducing TMZ into a variety of biocompatible polymer backbones are now possible, thus providing a platform for development a range of TMZ polymer therapeutics suitable for local and systemic chemotherapy. As extended and dose-dense TMZ regimens have shown clinical benefits, novel therapeutic modalities that augment the in vivo characteristics of TMZ stand to significantly improve the efficacy of chemotherapy for treating glioblastoma. Furthermore, functionalization of polymer therapeutics with biorecognition moieties hold promise for providing a mechanism for blood-brain barrier crossing of TMZ-containing polymers, including presentation of small molecules, peptides, and antibodies that facilitate transcytosis across the blood-brain barrier.

Various small molecule water soluble TMZ derivatives are also achievable, where the solubilizing group was a zwitterionic group (e.g., a phosphorylcholine group, a sulfobetaine group, or a carboxy betaine group), a glutathione group, a thiamine group, or poly(ethylene glycol) (e.g., one arm, two arm, and four arm derivatives). The synthesis of these derivatives is further described below. A general procedure for the preparation of water-soluble TMZ small molecule prodrugs with thioether linkages follows. TMZ prodrugs with covalent thioether linkages are prepared using this general strategy: TMZ-alkene (1 molar equivalent), the thiol-bearing species (e.g., phosphorylcholine thiol, carboxybetaine thiol, sulfobetaine thiol, glutathione, thiamine, or poly(ethylene glycol) thiol) (1 molar equivalent), and a radical photoinitiator (e.g., 2,2-dimethoxy-2-phenylacetophenone (DMPA)) are dissolved in an appropriate solvent, such as 2,2,2-trifluoroethanol for zwitterionic thiols, 0.1 M HCl for glutathione and thiamine-thiol, and DCM for poly(ethylene glycol) thiols. The reaction mixture is irradiated at room temperature under 365 nm light for 1 hour. The resulting small molecule prodrugs are purified by repeated precipitation into THF or diethyl ether or by reverse-phase high-pressure liquid chromatography. Polymeric prodrugs are purified by dialysis against appropriate organic solvents (e.g., DCM, THF, or 2,2,2-trifluoroethanol). Diagnostic spectroscopy of the depicted prodrugs confirming TMZ conjugation and retention of its labile chemical structure include anticipated $^1$H-NMR resonances corresponding to methyltriazene ($\delta$ ~3.88 ppm) and imidazole ($\delta$~8.88 ppm), as well as UV-Vis absorption at $\lambda$=323-325 nm.

TMZ prodrugs bearing a redox-sensitive disulfide linkage are prepared using the following general strategy: TMZ-pyridyl disulfide (1 molar equivalent) and the thiol-bearing molecule (1 molar equivalent) are dissolved in an appropriate solvent, such as 2,2,2-trifluoroethanol for zwitterionic thiols, 0.1 M HCl for glutathione and thiamine-thiol, and DCM for poly(ethylene glycol) thiols, containing a catalytic amount of acid (e.g., acetic acid) and stirred at room temperature for 16-24 hours. The resulting small molecule prodrugs are typically purified by repeated precipitation into tetrahydrofuran or diethyl ether; small molecule conjugates can also be purified by reverse-phase high-pressure liquid chromatography. Polymeric prodrugs are purified by dialysis against appropriate organic solvents (e.g., DCM, THF, or 2,2,2-trifluoroethanol). Spectroscopic characterization confirms successful TMZ conjugation, including $^1$H NMR resonances for the methyltriazene ($\delta$~3.88 ppm) and imidazole ($\delta$~8.88 ppm) groups, as well as a UV-Vis absorption maximum at $\lambda$=323-325 nm which confirms the presence of the intact heterocyclic structure.

Experimental details follow.

Materials.

2-Methacryloyloxyethyl phosphorylcholine (MPC), 2-hydroxyethyl methacrylate (HEMA), anhydrous acetonitrile, 4-(dimethylamino)pydridine (DMAP), N,N'-dicyclohexylcarbodiimide (DCC), sodium nitrite, dimethylsulfoxide (DMSO), sodium trifluoroacetate, 4-cyano-4-(phenylcarbonothioylthio)pentanoic acid, and 4,4'-azobis(4-cyanovaleric acid) (ACVA) were purchased from Sigma-Aldrich. Anhydrous diethyl ether, dichloromethane (DCM), ethyl acetate, hexanes, methanol (MeOH), ACN, concentrated sulfuric acid, tetrahydrofuran (THF) and hydrochloric acid (HCl) were purchased from Fisher Chemical. 2,2,2-trifluoroethanol (TFE) was purchased from Alfa Aesar. Temozolomide (TMZ) and 1-(3-dimethylaminopropyl)-3-ethylcarbodiimide hydrochloride (EDC) was purchased from TCI America. Deuterated solvents were purchased from Cambridge Isotope Laboratories, Inc. Unless otherwise noted, all chemicals were used as received without further purification. Inhibitor was removed from MPC prior to polymerizations according to known methods.

Instrumentation.

$^1$H-NMR (500 MHz), $^{13}$C-NMR (125 MHz), and $^{31}$P-NMR (202 MHz) spectra were collected using a Bruker Ascend 500 spectrometer equipped with a Prodigy cryoprobe. High-resolution mass spectra (HRMS) data were obtained using a JEOL-700 MStation spectrometer equipped with electron impact (EI) and fast atom bombardment (FAB) sources. UV-Vis absorption spectra were recorded on PerkinElmer Lambda 25 and Shimadzu 3600 spectrophotometers. Molecular weight and polydispersity (PDI) of copolymers 3A-3D were estimated by gel permeation chromatography (GPC) in TFE containing 0.02 M sodium trifluoroacetate against poly(methyl methacrylate) standards. GPC was operated at 1.0 ml/min and 40° C. with an Agilent 1260 isocratic pump, an autosampler, a PLgel guard column (50 mm×7.8 mm), two PLgel mixed C columns (300 mm×7.8 mm×5 mm), one PLgel mixed D column (300 mm×7.8 mm×5 mm), an Agilent 1260 refractive index detector, and an Agilent 1200 UV detector.

Synthesis of TMZ-Carboxylic Acid (1).

TMZ-carboxylic acid (shown as compound 1 in FIG. 1) was prepared following a previously described procedure. See, e.g., Arrowsmith, J.; Jennings, S. A.; Langnel, D. A. F.; Wheelhouse, R. T.; Stevens, M. F. G. Antitumour Imidazotetrazines. Part 39. Synthesis of Bis(Imidazotetrazines) with Saturated Space Groups. *J. Chem. Soc., Perkin Trans.* 2000, 1, 4432-4438. In a round bottom flask charged with a stir bar and fitted with an addition funnel, TMZ (2.29 grams, 11.8 millimoles) was dissolved in concentrated $H_2SO_4$ (23.6 milliliters), and the resulting yellow solution was cooled at 0° C. under nitrogen. A solution of sodium nitrite (2.51 grams, 36.4 millimoles) in water (23.6 milliliters) was then added drop-wise over 45 minutes, noting the evolution of a brown gas during addition. The mixture was allowed to warm to room temperature and was stirred under nitrogen, protected from light. After stirring for 17 hours, the solution was cooled at 0° C., and the reaction was quenched with ice (61.26 grams). Further stirring at 0° C. resulted in the precipitation of 1 as a fine white solid, which was isolated by vacuum filtration, washed with cold water, and dried under high vacuum to afford 1 in 75% yield. $^1$H-NMR (500 MHz, DMSO-$d_6$, δ, ppm): 3.88 (s, 3H), 8.82 (s, 1H), 13.33 (br, 1H). $^{13}$C-NMR (125 MHz, DMSO-$d_6$, δ, ppm): 36.32, 127.78, 129.09, 136.48, 139.10, 161.85. HRMS-EI (m/z): [M]$^+$ calculated for $C_6H_5N_5O_3$: 195.0392, found: 195.0395.

Synthesis of TMZ-Methacrylate (2).

In a round-bottom flask charged with a stir bar, compound 1 (592.5 mg, 3.05 mmol) was suspended in DCM (20 mL). HEMA (353 μL, 2.91 mmol) and catalytic DMAP (36.0 mg, 0.29 mmol) were added to the suspension, followed by EDC (674 mg, 3.51 mmol); the mixture became homogeneous and red. After stirring under nitrogen at room temperature for 14 hours, the mixture was filtered, and the filtrate was diluted with DCM (30 mL) and washed with aqueous 0.1 M HCl (5×50 mL). The organic layer was dried over Na2SO4 (s) and concentrated by rotary evaporation. The resulting white solid was dried under high vacuum, protected from light, to yield compound 2 in 71% yield. 1H-NMR (500 MHz, DMSO-d6, δ, ppm): 1.87 (s, 3H), 3.88 (s, 3H), 4.43 (t, J=5 Hz, 2H), 4.62 (t, 2H), 5.68 (s, 1H), 6.04 (s, 1H), 8.85 (s, 1H). 13C (125 MHz, DMSO-d6, δ, ppm): 17.93, 36.40, 62.49, 62.51, 126.15, 126.20, 129.41, 135.60, 136.87, 138.93, 160.29, 166.41. HRMS-FAB (m/z): [M+H]$^+$ calculated for $C_{12}H_{14}N_5O_5$: 308.0995, found: 308.0989.

General Procedure for the Synthesis of Copolymers 3A-3D by RAFT.

MPC and compound 2 were dissolved in TFE at a total monomer concentration of 1 molar in a 20 milliliter vial charged with a stir bar. ACVA and 4-cyano-4-(phenylcarbonothioylthio)pentanoic acid were added as radical initiator (I) and chain-transfer agent (CTA), respectively, targeting [monomer]$_0$:[CTA]$_0$:[I]$_0$=68:5:1. The reaction solution was purged with nitrogen at 0° C. for 15 minutes, and then was stirred at 70° C. to initiate polymerization, gauging monomer conversion by $^1$H-NMR spectroscopy. After achieving monomer conversion greater than 88%, the polymerization was allowed to cool to room temperature and was quenched by exposure to air. The crude reaction mixture was precipitated from TFE into THF (repeated three times) to remove unreacted monomer 2, and the polymer was isolated by centrifugation. The polymer pellet was dissolved in aqueous 0.1 M hydrochloric acid (10 milliliters), added to a 10,000 molecular weight cutoff (MWCO) centrifugal dialysis membrane, and centrifuged (4000×g, 20 minutes, room temperature). Filtrate was discarded, and centrifugal dialysis was repeated two more times. Concentrated polymer was dissolved in aqueous 0.1 molar hydrochloric acid (3 milliliters), and lyophilization afforded polymers 3A-3D as pink solids. Incorporation of TMZ-methacrylate 2 was estimated by $^1$H-NMR spectroscopy by comparing relative signal intensities at 8.46 ppm (C—H in TMZ) and 2.80-3.30 ppm (N—(CH$_3$)$_3$ in MPC). Copolymer yields were 60-74%. $^1$H-NMR (500 MHz, TFE-d$_3$, δ, ppm): 0.08-1.09 (br, 3H), 1.09-2.15 (br, 2H), 3.05 ppm (s, 9H), 3.54 (br, 2H), 3.88 (s, 3H), 4.06 (br, 4H), 4.32 (br, 2H), 4.52 (br, 4H), 8.46 (s, 1H). $^{13}$C-NMR (125 MHz, TFE-d$_3$, δ, ppm): 18.32, 19.81, 38.03, 46.54, 47.17, 55.97, 64.24, 64.99, 65.91, 66.68, 68.09, 128.59, 131.41, 138.82, 140.88, 162.72, 180.09. $^{31}$P-NMR (202 MHz, TFE-d$_3$, δ, ppm): −2.36.

Measurement of TMZ-Methacrylate Incorporation by UV-Vis Spectroscopy.

TMZ-methacrylate 2 was dissolved in TFE at concentrations ranging from 0.0005 mg/ml to 0.025 mg/ml, and a calibration curve was constructed from UV-Vis absorbance values at 323 nm. PolyMPC-TMZ copolymers 3A-3D were dissolved at a concentration of 0.05 mg/ml, and UV-Vis absorbance values were measured at 323 nm. Mass incorporation of compound 2 was then determined using the calibration curve.

Synthesis of Hydroxyethyl Pyridyl Disulfide.

To a round bottom flask containing a solution of Aldrithiol™-2 (8.43 g, 38.4 mmol) and acetic acid (732 μL, 12.8 mmol) in methanol (0.3 M) was added mercaptoethanol (1.8 mL, 25.6 mmol). The mixture was stirred for 24 hours at room temperature, then filtered to remove the thione by-product and concentrated by rotary evaporation. The crude product was purified by column chromatography over silica gel, eluting with ethyl acetate/hexanes (30/70-40/60-50/50-60/40), to yield 2-(2-(pyridin-2-yl)diuslfanyl)ethanol as a yellow oil. $^1$H NMR (MeOD, 500 MHz): δ 2.96 (t, J=7.5 Hz, 2H), 3.79 (t, J=7.5 Hz, 2H), 7.22-7.25 (m, 1H), 7.79-7.86 (m, 2H), 8.42 (d, J=6 Hz, 1H) ppm. $^{13}$C NMR (MeOD, 125 MHz) δ 148.96, 137.96, 121.04, 120.12, 59.20, 41.22 ppm.

Synthesis of TMZ-Substituted Pyridyl Disulfide.

In a vial charged with a stir bar, 2-hydroxyethyl 2-pyridyl disulfide (714.2 mg, 3.8 mmol), TMZ-COOH (815 mg, 4.20 mmol), and 4-dimethylaminopyridine (DMAP) (43.0 mg, 0.35 mmol) were suspended in dichloromethane (DCM) (25 mL). 1-Ethyl-3-(3-dimethylaminopropyl)carbodiimide (EDC) (1.1 g, 5.7 mmol) was added and the suspension was stirred at room temperature. After 24 hours, the mixture was concentrated by rotary evaporation, then purified by passing through silica gel, eluting with ethyl acetate:hexanes (50: 50-60:40-70:30-80:20-90:10-100:0). Product fractions were combined and concentrated by rotary evaporation. Vacuum drying afforded TMZ-PDS as a white solid in 58% yield. $^1$H-NMR (500 MHz, DMSO-$d_6$, δ, ppm): 3.27 (t, J=6 Hz), 3.90 (s), 4.56 (t, J=6 Hz), 7.22 (dd, J=10 Hz), 7.76 (td), 7.88 (d, J=5 Hz), 8.45 (d, 5 Hz), 8.88 (s). $^{13}$C-NMR (125 MHz, DMSO-$d_6$, δ, ppm): 36.42, 36.94, 62.16, 119.27, 121.21, 126.15, 129.43, 136.85, 137.80, 138.93, 149.52, 158.96, 160.16.

Synthesis of N-Allyl Substituted TMZ.

In a typical reaction, TMZ-COOH (1.05 molar equivalents), allylamine (1 molar equivalent), and DMAP (0.1 molar equivalents) are suspended in DCM. EDC (1.5 molar equivalents) is added and the suspension is stirred at room temperature. After 16-24 hours, the mixture is concentrated by rotary evaporation and passed through a silica gel column eluting with a mixture of ethyl acetate:hexanes. Allyl-TMZ is isolated by vacuum filtration as a white solid. $^1$H-NMR (500 MHz, DMSO-$d_6$, δ, ppm): 3.86 (s), 3.92, 5.08 (d, 10-11 Hz), 5.15 (d, 17 Hz), 5.89 (m), 8.64 (s), 8.85 (s).

Synthesis of TMZ-Pentafluorophenyl Ester.

In a typical reaction, TMZ-COOH (1.2 molar equivalents), pentafluorophenol (1 molar equivalents), and DMAP (0.1 molar equivalents) are suspended in DCM. EDC hydrochloride (1.5 molar equivalents) is added, and the suspension is stirred at room temperature. After 16-24 h, the reaction mixture is concentrated by rotary evaporation and purified by column chromatography over silica gel, eluting with a mixture of ethyl acetate/hexanes.

Synthesis of Thiamine Bromide.

In a typical reaction, to a solution of thiamine (1 molar equivalents) in DCM (0.2 M) is added phosphorus tribromide (1 equivalents) at 0° C. This mixture is stirred at room temperature for 16-24 h, and the product isolated by precipitation into diethyl ether or related organic solvents.

Synthesis of Thiamine Thiol.

In a typical reaction, potassium thioacetate (1 molar equivalents) is added to a solution of Thiamine-Br (1 molar equivalent) in DMF, and the solution is stirred at room temperature. The reaction mixture is purified by precipitation into an organic solvent (e.g., diethyl ether) to yield Thiamine-SAc which is then deprotected by the addition of a primary amine (e.g., butylamine, 10 molar equivalents) in an appropriate organic solvent (e.g., DMF) at room temperature. Purification by precipitation into an organic solvent (e.g., diethyl ether) yields Thiamine-SH.

Synthesis of Phosphorylholine Thiol.

PC-thiol is prepared following a modified literature procedure: 2-hydroxyethyl disulfide (1 molar equiv.) and triethylamine (2.5 molar equiv.) are dissolved in anhydrous tetrahydrofuran (1.0 M) and added to a solution of 2-chloro-1,3,2-dioxaphospholane-2-oxide (2.5 molar equiv.) at −20° C. The reaction mixture is stirred at room temperature for 2 h, then filtered under nitrogen atmosphere and concentrated by rotary evaporation to give the bis-substituted phospholane. Successful substitution and retention of the ring structure is confirmed by $^{31}$P NMR spectroscopy with a characteristic resonance at ~17 ppm corresponding to the phosphorus atom of the intact ring. The bis-substituted phospholane is then combined with trimethylamine (TMA, 6 molar equiv.) in anhydrous acetonitrile (2.0 M) at 0° C. in a pressure vessel. The reaction mixture is heated to 70° C. for 24 h, then cooled and filtered to give the PC-disulfide intermediate. $^{31}$P NMR spectroscopy confirmed successful ring-opening by TMA by a resonance at ~0 ppm corresponding to the phosphate. The PC-disulfide is then reduced to the thiol by dissolution in methanol and mixing with agarose beads containing immobilized tris(2-carboxyethyl) phosphine. The beads are removed by filtration, and precipitation into an organic solvent such as diethyl ether yields the desired PC-SH.

Synthesis of Sulfobetaine Thiol and Carboxybetaine Thiol.

SB-thiol and CB-thiol are prepared by nucleophilic ring opening reactions of 1,3-propane sultone and β-propiolactone, respectively, using bis(2-dimethylaminoethyl) disulfide dihydrochloride (DMAEDS). 1,3-Propane sultone (10 molar equivalents) is dissolved in anhydrous acetonitrile (1.0 M) with DMAEDS (1 molar equivalents) and triethylamine (10 molar equivalents). The reaction is heated to reflux for several hours and the product obtained is washed with anhydrous acetonitrile to yield SB-disulfide. $^1$H NMR spectroscopy confirms the desired product by the resonance corresponding to the cationic dimethylamine protons (δ~3.2 ppm), as well as by mass spectroscopy. The disulfide product is then dissolved in methanol and mixed with agarose beads containing immobilized tris(2-carboxyethyl) phosphine to reduce the disulfide. Following the reduction, the beads are removed by filtration, and precipitation of the mixture into an appropriate organic solvent, such as diethyl ether, yields SB-SH. NMR spectroscopy confirms the reduction of the disulfide and mass spectroscopy characterizes the molecular weight of the desired product.

The compounds, polymers, and methods of the present disclosure include at least the following embodiments, which are non-limiting.

Embodiment 1

A temozolomide compound of structure (I)

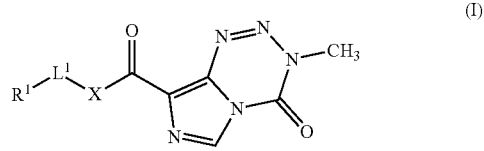

wherein X is —O— or —NR$^a$—, wherein R$^a$ is hydrogen or a $C_{1-6}$ alkyl group; L$^1$ is a divalent $C_{1-12}$ alkylene group, di($C_{2-12}$ alkylene) disulfide group, $C_{2-12}$ alkylene ester group, $C_{6-20}$ arylene group, $C_{1-20}$ alkylene oxide group, or $C_{1-12}$ alkylene sulfide group; n is 0 or 1; and R$^1$ is a group of the formula H$_2$C=C(R$^b$)—(C=O)—W—, wherein R$^b$ is methyl, hydrogen, fluoro, cyano, or trifluoromethyl, and W is —O— or —NH—; an alkenyl group; an alkynyl group; an aldehyde group; a ketone group; a thiol group; a pentafluorophenyl group, a pyridyl disulfide group, a zwitterionic group, a glutathione group, a thiamine group, or a poly (ethylene glycol) group.

Embodiment 2

The temozolomide compound of embodiment 1, wherein R$^1$ is of the formula wherein in the above formulas, $R^5$ is hydrogen or a $C_{1-6}$ alkyl group; $R^d$ is hydrogen or a $C_{1-6}$ alkyl group; m is an integer from greater than 1 to 900, or 1 to 500, or 1 to 250, or 1 to 100, or 1 to 50; A is a center of permanent positive charge or a center of permanent negative charge; B is a divalent group comprising a $C_{1-12}$ alkylene group, a $C_{6-30}$ arylene or heteroarylene group, or an alkylene oxide group; and C is a center of permanent positive charge or a center of permanent negative charge, provided that the zwitterionic group has an overall net charge of zero.

Embodiment 3

The temozolomide compound of embodiment 1, wherein X is —O— or —NH—; n is 1; $L^1$ is a divalent $C_{1-6}$ alkylene group; and $R^1$ is a methacrylate group or an acrylate group or acrylamide group.

Embodiment 4

The temozolomide compound of embodiment 1, wherein X is —O— or —NH—; n is 1; $L^1$ is a divalent di($C_{1-6}$ alkylene) disulfide group; and $R^1$ is a methacrylate group.

Embodiment 5

The temozolomide compound of embodiment 1, wherein X is —O— or —NH—; n is 1; $L^1$ is a divalent $C_{1-6}$ alkylene group; and $R^1$ is a methacrylamide group.

Embodiment 6

The temozolomide compound of embodiment 1, wherein X is —O—; n is 1; $L^1$ is a divalent $C_{1-6}$ alkylene group; and $R^1$ is an aldehyde group or a ketone group.

Embodiment 7

The temozolomide compound of embodiment 1, wherein X is —O—; n is 1; $L^1$ is a divalent $C_{1-6}$ alkylene group; and $R^1$ is a thiol group.

Embodiment 8

The temozolomide compound of embodiment 1, wherein X is —NH—; n is 1; $L^1$ is a divalent $C_{1-6}$ alkylene group; and $R^1$ is a vinyl group.

Embodiment 9

The temozolomide compound of embodiment 1, wherein X is —NH—; n is 1; $L^1$ is a divalent $C_{1-6}$ alkylene group; and $R^1$ is an ethynyl group.

Embodiment 10

The temozolomide compound of embodiment 1, wherein X is —O—; n is 0; and $R^1$ is a pentafluorophenyl group.

Embodiment 11

The temozolomide compound of embodiment 1, wherein X is —O—; n is 1; $L^1$ is a divalent $C_{1-6}$ alkylene group; and $R^1$ is a pyridyl disulfide group.

Embodiment 12

The temozolomide compound of embodiment 1, wherein X is —O—; n is 1; $L^1$ is a divalent $C_{1-12}$ alkylene sulfide group or a divalent $C_{1-6}$ alkylene group; and $R^1$ is a glutathione group.

Embodiment 13

The temozolomide compound of embodiment 1, wherein X is —NH—; n is 1; $L^1$ is a divalent $C_{1-6}$ alkylene group; and $R^1$ is a thiamine group.

Embodiment 14

The temozolomide compound of embodiment 1, wherein X is —O—; n is 1; $L^1$ is a di($C_{2-12}$ alkylene) disulfide group or $C_{1-12}$ alkylene sulfide group; and $R^1$ is a poly(ethylene glycol) group.

Embodiment 15

The temozolomide compound of embodiment 1, wherein X is —O— or —NH—; n is 1; $L^1$ is a divalent di($C_{2-12}$ alkylene) disulfide group, $C_{2-12}$ alkylene ester group, $C_{6-20}$ arylene group, $C_{1-20}$ alkylene oxide group, or $C_{1-12}$ alkylene sulfide group; and $R^1$ is a phosphorylcholine zwitterionic group having the structure A-B-C-, wherein A is an ammonium group of the formula —N($R^7$)$_3$, wherein $R^7$ is a $C_{1-6}$ alkyl group; B is a divalent $C_{1-6}$ alkylene group; and C is a divalent phosphate group.

Embodiment 16

The temozolomide compound of embodiment 1, wherein X is —O— or —NH—; n is 1; $L^1$ is a divalent $C_{1-6}$ alkylene group; and $R^1$ is a sulfobetaine zwitterionic group having the structure A-B-C-$L^2$-, wherein A is a sulfonate group; B is a divalent $C_{1-6}$ alkylene group; C is a divalent ammonium group; and $L^2$ is a divalent $C_{1-6}$ alkylene group; wherein $L^2$ of the zwitterionic group is covalently bound to $L^1$ through a thioether bond or a disulfide bond.

Embodiment 17

The temozolomide compound of embodiment 1, wherein X is —O— or —NH—; n is 1; $L^1$ is a divalent $C_{1-6}$ alkylene group; and $R^1$ is a carboxybetaine zwitterionic group having the structure A-B-C-$L^2$-, wherein A is a carboxylate group; B is a divalent $C_{14}$ alkylene group; C is a divalent ammonium group; and $L^2$ is a divalent $C_{1-6}$ alkylene group; wherein $L^2$ of the zwitterionic group is covalently bound to $L^1$ through a thioether bond or a disulfide bond.

Embodiment 18

The temozolomide compound of embodiment 1, wherein $R^1$ is a group of the formula $H_2C=C(R^b)$—(C=O)—W—, wherein $R^b$ is methyl, hydrogen, fluoro, cyano, or trifluoromethyl, and W is —O— or —NH—; an alkenyl group; an alkynyl group; an aldehyde group; a ketone group; a thiol group, a pentafluorophenyl group, or a pyridyl disulfide group.

Embodiment 19

A polymer comprising repeating units comprising temozolomide derived from the temozolomide compound of embodiment 18; and optionally, repeating units of formula (II), formula (III), or a combination thereof

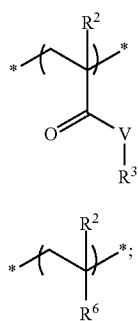

wherein in each occurrence of the repeating units of formula (II) $R^2$ is a hydrogen or a $C_{1-6}$ alkyl group; V is —O— or —NH—; and $R^3$ is a zwitterionic group, a poly($C_{1-6}$ alkylene oxide) group, a hydroxy-substituted $C_{1-6}$ alkyl group, or a $C_{1-12}$ alkyl group; and wherein in each occurrence of the repeating units of formula (III) $R^2$ is a hydrogen or a $C_{1-6}$ alkyl group; and $R^6$ is a $C_{6-20}$ aryl group.

Embodiment 20

The polymer of embodiment 19, wherein the polymer is a copolymer comprising repeating units of formula (II), and wherein $R^3$ is a zwitterion having the structure -$L^2$-A-B-C; wherein $L^2$ is a divalent $C_{1-12}$ alkylene group, $C_{6-20}$ arylene group, or $C_{1-20}$ alkylene oxide group; A is a center of permanent positive charge or a center of permanent negative charge; B is a divalent group comprising a $C_{1-12}$ alkylene group, a $C_{6-30}$ arylene or heteroarylene group, or a $C_{1-20}$ alkylene oxide group; and C is a center of permanent positive charge or a center of permanent negative charge, provided that the zwitterion has an overall net charge of zero.

Embodiment 21

The polymer of embodiment 19 or 20, wherein the polymer is a copolymer comprising repeating units of formula (II), and wherein $R^3$ is a zwitterionic group of the formula

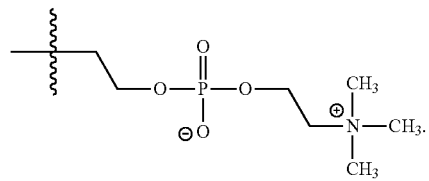

Embodiment 22

The polymer of any one of embodiments 19 to 21, wherein the repeating units comprising temozolomide are of formula (IV)

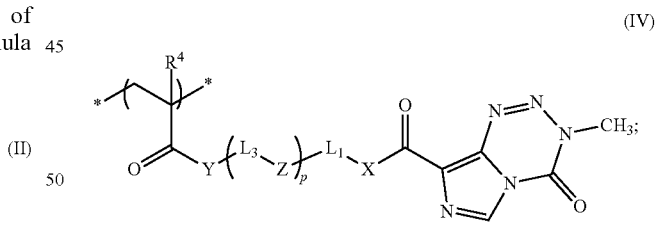

wherein R is independently at each occurrence a hydrogen or a $C_{1-6}$ alkyl group; Y is independently at each occurrence —O— or —NH—; $L^3$ is independently at each occurrence a divalent $C_{1-12}$ alkylene group, di($C_{1-12}$ alkylene) disulfide group, $C_{1-12}$ alkylene ester group, $C_{6-20}$ arylene group, or $C_{1-20}$ alkylene oxide group; Z is independently at each occurrence a disulfide group, a thioether group, a triazole group, a hydrazone group, or an amide group; $L^1$ is independently at each occurrence a divalent $C_{1-12}$ alkylene group, di($C_{1-12}$) alkylene disulfide group, $C_{1-12}$ alkylene ester group, $C_{6-20}$ arylene group, $C_{1-20}$ alkylene oxide group, or $C_{1-12}$ alkylene sulfide group; X is independently at each occurrence —O— or —NH—; and p is independently at each occurrence 0 or 1.

Embodiment 23

The polymer of embodiment 22, wherein the polymer is a copolymer comprising repeating units of formula (II) and (IV), wherein in each occurrence of the repeating units of formula (II), $R^2$ is a methyl group; V is —O—; and $R^3$ is a phosphorylcholine group having the structure

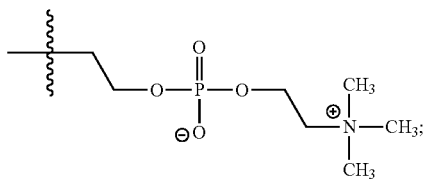

and in each occurrence of the repeating units of formula (IV), $R^4$ is a methyl group; Y is —O—; p is 0; $L^1$ is a divalent $C_{1-6}$ alkylene group; and X is —O—.

Embodiment 24

The polymer of embodiment 22, wherein the polymer is a copolymer comprising repeating units of formula (II) and (IV), wherein in each occurrence of the repeating units of formula (II), $R^2$ is a methyl group; V is —O—; and $R^2$ is a phosphorylcholine group having the structure

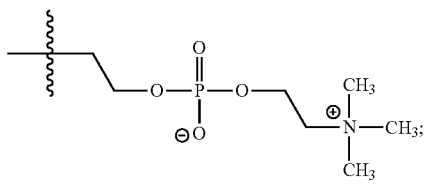

and in each occurrence of the repeating units of formula (IV), $R^4$ is a methyl group; Y is —O—; p is 0; $L^1$ is a divalent di($C_{1-6}$ alkylene) disulfide group; and X is —O—.

Embodiment 25

The polymer of embodiment 22, wherein the polymer is a copolymer comprising repeating units of formula (II) and (IV), wherein in each occurrence of the repeating units of formula (II), $R^2$ is a methyl group; V is —O—; and $R^2$ is a phosphorylcholine group having the structure

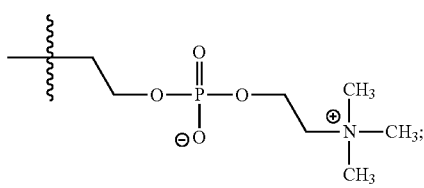

and in each occurrence of the repeating units of formula (IV), $R^4$ is a methyl group; Y is —O—; p is 1; $L^3$ is a divalent $C_{1-6}$ alkylene group; Z is a $C_{1-6}$ thioether group; $L^1$ is a divalent $C_{1-6}$ alkylene group; and X is —NH—.

Embodiment 26

The polymer of embodiment 22, wherein the polymer is a copolymer comprising repeating units of formula (II) and (IV), wherein in each occurrence of the repeating units of formula (II), $R^2$ is a methyl group; V is —O—; and $R^2$ is a phosphorylcholine group having the structure

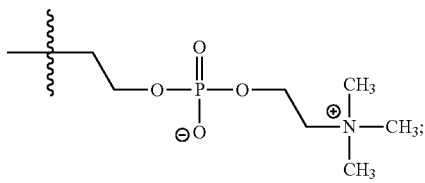

and in each occurrence of the repeating units of formula (IV), $R^4$ is a methyl group; Y is —O—; p is 1; $L^3$ is a divalent $C_{1-20}$ alkylene oxide group; Z is a triazole group of the formula

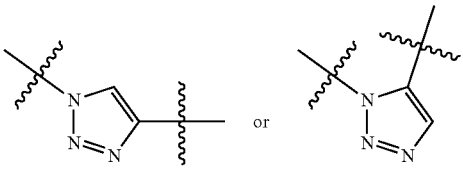

$L^1$ is a divalent $C_{1-6}$ alkylene group; and X is —NH—.

Embodiment 27

The polymer of embodiment 22, wherein the polymer is a copolymer comprising repeating units of formula (II) and (IV), wherein in each occurrence of the repeating units of formula (II), $R^2$ is a methyl group; V is —O—; and $R^2$ is a phosphorylcholine group having the structure

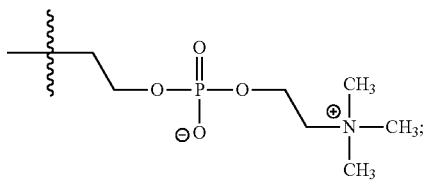

and in each occurrence of the repeating units of formula (IV), $R^4$ is a methyl group; Y is —O—; p is 1; $L^3$ is a divalent $C_{1-6}$ alkylene group; Z is a hydrazone group of the formula —(C=O)—NH—N=CH—; $L^1$ is a divalent $C_{1-6}$ alkylene group; and X is —O—.

Embodiment 28

The polymer of embodiment 22, wherein the polymer is a copolymer comprising repeating units of formula (II) and (IV), wherein in each occurrence of the repeating units of formula (II), $R^2$ is a methyl group; V is —O—; and $R^2$ is a phosphorylcholine group having the structure

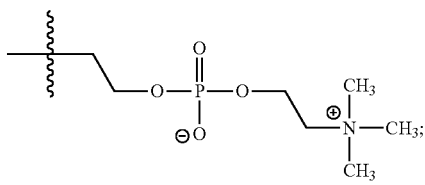

and in each occurrence of the repeating units of formula (IV), $R^4$ is a methyl group; Y is —O—; p is 0; $L^1$ is a divalent $C_{1-6}$ alkylene group; and X is —NH—.

Embodiment 29

The polymer of embodiment 22, wherein the polymer is a copolymer comprising repeating units of formula (II) and (IV), wherein in each occurrence of the repeating units of formula (II), $R^2$ is a methyl group; V is —O—; and $R^2$ is a phosphorylcholine group having the structure

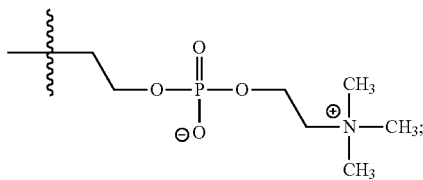

and in each occurrence of the repeating units of formula (IV), $R^4$ is a methyl group; Y is —O—; p is 1; $L^3$ is a divalent $C_{1-12}$ alkylene group; Z is a disulfide group; $L^1$ is a divalent $C_{1-6}$ alkylene group; and X is —O—.

Embodiment 30

The polymer of any one of embodiments 19 to 29, wherein the polymer comprises 1 to 100 mole percent of repeating units comprising temozolomide based on the total repeating units of the polymer.

Embodiment 31

A poly(ethylene glycol)-temozolomide conjugate comprising a poly(ethylene glycol) having at least two chain ends conjugated to a temozolomide compound.

Embodiment 32

The poly(ethylene glycol)-temozolomide conjugate of embodiment 31, wherein the poly(ethylene glycol) having at least two chain ends conjugated to a temozolomide compound is of formula (V) or (VI)

$C_{1-12}$ alkylene ester group, $C_{6-20}$ arylene group, $C_{1-20}$ alkylene oxide group, or $C_{1-12}$ alkylene sulfide group; and q is an integer from 1 to 50.

Embodiment 33

A method of treating a disease, the method comprising administering a therapeutically effective amount of a composition comprising the polymer of any one of embodiments 19 to 29, the poly(ethylene glycol)-temozolomide conjugate of embodiments 31 or 32, or the temozolomide compound of any one of embodiments 12 to 17.

Embodiment 34

A polymer nanoparticle comprising a polymer of any one of embodiments 20 to 29.

Embodiment 35

The polymer nanoparticle of embodiment 34, wherein the polymer is a block copolymer or a random copolymer.

Embodiment 36

The polymer nanoparticle of embodiment 34 or 35, wherein the polymer nanoparticle further comprises a therapeutic moiety encapsulated in the core of the nanoparticle.

Embodiment 37

The polymer nanoparticle of embodiment 36, therein the therapeutic moiety comprises temozolomide, 06-benzylguanine, doxorubicin, or a combination comprising at least one of the foregoing.

Embodiment 38

A method of treating a disease, the method comprising administering a therapeutically effective amount of a composition comprising a plurality of polymer nanoparticles according to any one or more of embodiments 34 to 37.

All cited patents, patent applications, and other references are incorporated herein by reference in their entirety. However, if a term in the present application contradicts or

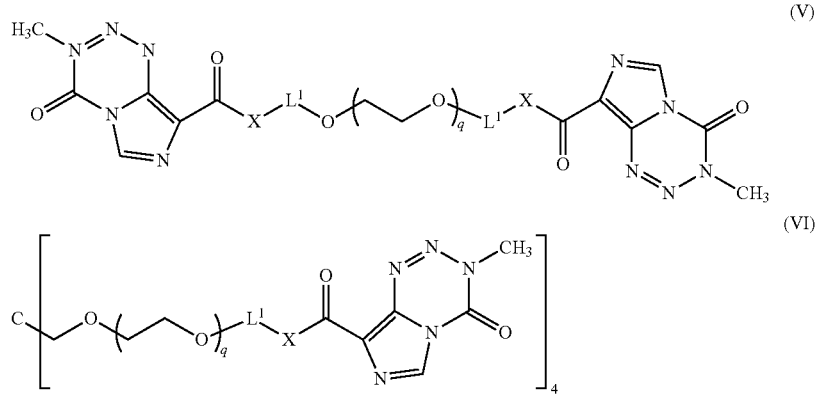

wherein X is independently at each occurrence —O— or —NH—; $L^1$ is independently at each occurrence a divalent $C_{1-12}$ alkylene group, di($C_{1-12}$ alkylene) disulfide group, conflicts with a term in the incorporated reference, the term from the present application takes precedence over the conflicting term from the incorporated reference.

All ranges disclosed herein are inclusive of the endpoints, and the endpoints are independently combinable with each other. Each range disclosed herein constitutes a disclosure of any point or sub-range lying within the disclosed range.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or" unless clearly stated otherwise. Further, it should further be noted that the terms "first," "second," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

The term "alkyl" means a branched or straight chain, unsaturated aliphatic hydrocarbon group, e.g., methyl, ethyl, n-propyl, i-propyl, n-butyl, s-butyl, t-butyl, n-pentyl, s-pentyl, and n- and s-hexyl. "Alkenyl" means a straight or branched chain, monovalent hydrocarbon group having at least one carbon-carbon double bond (e.g., ethenyl (—HC=CH$_2$)). "Alkoxy" means an alkyl group that is linked via an oxygen (i.e., alkyl-O—), for example methoxy, ethoxy, and sec-butyloxy groups. "Alkylene" means a straight or branched chain, saturated, divalent aliphatic hydrocarbon group (e.g., methylene (—CH$_2$—) or, propylene (—(CH$_2$)$_3$—)). "Cycloalkylene" means a divalent cyclic alkylene group, —C$_n$H$_{2n-x}$, wherein x is the number of hydrogens replaced by cyclization(s). "Cycloalkenyl" means a monovalent group having one or more rings and one or more carbon-carbon double bonds in the ring, wherein all ring members are carbon (e.g., cyclopentyl and cyclohexyl). "Aryl" means an aromatic hydrocarbon group containing the specified number of carbon atoms, such as phenyl, tropone, indanyl, or naphthyl. The prefix "halo" means a group or compound including one more of a fluoro, chloro, bromo, or iodo substituent. A combination of different halo groups (e.g., bromo and fluoro), or only chloro groups can be present. The prefix "hetero" means that the compound or group includes at least one ring member that is a heteroatom (e.g., 1, 2, or 3 heteroatom(s)), wherein the heteroatom(s) is each independently N, O, S, Si, or P. "Substituted" means that the compound or group is substituted with at least one (e.g., 1, 2, 3, or 4) substituents that can each independently be a C$_{1-9}$ alkoxy, a C$_{1-9}$ haloalkoxy, a nitro (—NO$_2$), a cyano (—CN), a C$_{1-6}$ alkyl sulfonyl (—S(=O)$_2$-alkyl), a C$_{6-12}$ aryl sulfonyl (—S(=O)$_2$-aryl)a thiol (—SH), a thiocyano (—SCN), a tosyl (CH$_3$C$_6$H$_4$SO$_2$—), a C$_{3-12}$ cycloalkyl, a C$_{2-12}$ alkenyl, a C$_{5-12}$ cycloalkenyl, a C$_{6-12}$ aryl, a C$_{7-13}$ arylalkylene, a C$_{4-12}$ heterocycloalkyl, and a C$_{3-12}$ heteroaryl instead of hydrogen, provided that the substituted atom's normal valence is not exceeded. The number of carbon atoms indicated in a group is exclusive of any substituents. For example —CH$_2$CH$_2$CN is a C$_2$ alkyl group substituted with a nitrile.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. A temozolomide compound of structure (I)

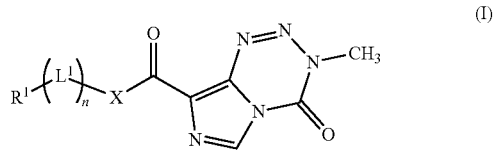

wherein
X is —O—;
L$^1$ is a divalent C$_{1-6}$ alkylene group;
n is 1; and
R$^1$ is an aldehyde group.

2. A temozolomide compound of structure (I)

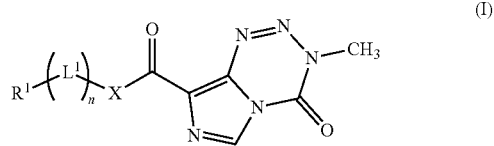

wherein
X is —O—;
L$^1$ is a divalent C$_{1-6}$ alkylene group;
n is 1; and
R$^1$ is a ketone group of the formula

wherein R$^5$ is a C$_{1-6}$ alkyl group.

* * * * *